(12) United States Patent
Samsoondar

(10) Patent No.: US 7,807,450 B2
(45) Date of Patent: *Oct. 5, 2010

(54) PLASMA EXTRACTION APPARATUS

(75) Inventor: James Samsoondar, Markham (CA)

(73) Assignee: Chromedx Inc., Markham, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/835,631

(22) Filed: Aug. 8, 2007

(65) Prior Publication Data

US 2007/0284298 A1 Dec. 13, 2007

Related U.S. Application Data

(63) Continuation-in-part of application No. 11/432,616, filed on May 12, 2006.

(51) Int. Cl.
*C12M 3/00* (2006.01)

(52) U.S. Cl. .................................. 435/287.3

(58) Field of Classification Search .............. None
See application file for complete search history.

(56) References Cited

U.S. PATENT DOCUMENTS

| | | | | |
|---|---|---|---|---|
| 3,874,850 | A * | 4/1975 | Sorensen et al. | 436/50 |
| 4,013,417 | A | 3/1977 | Raffaele | |
| 4,668,399 | A * | 5/1987 | Duggins | 210/637 |
| 4,849,340 | A * | 7/1989 | Oberhardt | 435/13 |
| 5,725,774 | A * | 3/1998 | Neyer | 210/645 |
| 5,976,433 | A * | 11/1999 | Komatsu et al. | 264/41 |
| 6,348,156 | B1 * | 2/2002 | Vishnoi et al. | 210/739 |
| 6,597,438 | B1 * | 7/2003 | Cabuz et al. | 356/39 |
| 7,018,838 | B2 * | 3/2006 | Murphy et al. | 435/325 |
| 7,258,774 | B2 * | 8/2007 | Chou et al. | 204/450 |
| 7,682,833 | B2 * | 3/2010 | Miller et al. | 436/165 |
| 2002/0045272 | A1 | 4/2002 | McDevitt et al. | |
| 2002/0091057 | A1 * | 7/2002 | Westberg et al. | 494/45 |
| 2002/0100714 | A1 | 8/2002 | Staats | |
| 2002/0143437 | A1 | 10/2002 | Handique et al. | |
| 2002/0197167 | A1 * | 12/2002 | Kornelsen | 417/53 |
| 2004/0224362 | A1 * | 11/2004 | Gjerde et al. | 435/7.1 |
| 2005/0130292 | A1 | 6/2005 | Ahn et al. | |
| 2005/0233352 | A1 * | 10/2005 | Zoval | 435/6 |

OTHER PUBLICATIONS

Office Action issued in connection with co-pending U.S. Appl. No. 11/108,912, filed on Apr. 19, 2005 (retrievable from PAIR), mailed on Jul. 10, 2008.
Office Action issued in connection with co-pending U.S. Appl. No. 11/103,619, filed on Apr. 12, 2005 (retrievable from PAIR), mailed on Jun. 25, 2008.
Office Action issued in connection with co-pending U.S. Appl. No. 11/415,284, filed on May 2, 2006 (retrievable from PAIR), mailed on Aug. 5, 2008.
Co-pending U.S. Appl. No. 11/432,616, "Diagnostic Whole Blood and Plasma Apparatus", May 12, 2006. (Retrievable from PAIR).
Co-pending U.S. Appl. No. 11/466,588, "Hollow Needle Assembly", Filed Aug. 23, 2006. (Retrievable from PAIR).
Co-pending U.S. Appl. No. 11/738,889, "Hollow Needle Assembly" (CIP), Filed Apr. 23, 2007. (Retrievable from PAIR).
Co-pending U.S. Appl. No. 12/016,315, "Spectroscopic Sample Holder" CIP, Filed Jan. 18, 2008. (Retrievable from PAIR).
Co-pending U.S. Appl. No. 11/108,912, "Joint-Diagnostic Spectroscopic and Biosensor Cartridge", Filed Apr. 19, 2005. (Retrievable from PAIR).
Co-pending U.S. Appl. No. 11/415,284, "Joint-Diagnostic Spectroscopic and Biosensor Meter" CIP, filed May 2, 2006 (Retrievable from PAIR).
Co-pending U.S. Appl. No. 11/103,619, "Blood Collection and Measurement Apparatus", Filed Apr. 12, 2005, (Retrievable from PAIR).
Office Action issued in connection with co-pending U.S. Appl. No. 11/103,619, filed on Apr. 12, 2005, mailed on Jan. 5, 2009 (retrievable from Pair).
Office Action issued in connection with co-pending U.S. Appl. No. 11/415,284, filed on May 2, 2006, mailed on Jan. 23, 2009 (retrievable from Pair).
Office Action issued in connection with co-pending U.S. Appl. No. 11/466,588, filed on Aug. 23, 2006, mailed on Feb. 20, 2009 (retrievable from Pair).
Office Action issued in connection with co-pending U.S. Appl. No. 11/432,616, filed on May 12, 2006 (retrievable from Pair), mailed on Oct. 7, 2008.

(Continued)

*Primary Examiner*—Ann Y Lam
(74) *Attorney, Agent, or Firm*—Ian C. McMillan; Bereskin & Parr LLP/S.E.N.C.R.L., s.r.l.

(57) ABSTRACT

A system that is suitable for extracting plasma from blood received from a blood supply is provided. The system comprises a housing, an inlet opening for receiving the blood, a filtration chamber comprising a membrane, and a plasma compartment. The membrane forms a barrier between the blood and the plasma extracted from the blood, and the plasma compartment collects the plasma extracted from the blood. In some embodiments, the system comprises a plasma flow path compression chamber for pulling plasma across the membrane. In some embodiments, the system comprises a blood flow path compression chamber for facilitating blood flow. Some embodiments of the system further comprise means for measuring plasma and blood analytes using spectroscopic and biosensor techniques.

26 Claims, 22 Drawing Sheets

OTHER PUBLICATIONS

Response filed in connection with co-pending U.S. Appl. No. 11/103,619, filed on Apr. 12, 2005 (retrievable from Pair).
Office Action issued in connection with co-pending U.S. Appl. No. 12/016,315, filed on Jan. 18, 2008 (retrievable from Pair), mailed on Oct. 20, 2008.
Office Action issued in connection with co-pending U.S. Appl. No. 11/432,616 (retrievable from Pair), mailed on Sep. 17, 2009.
Office Action issued in connection with co-pending U.S. Appl. No. 12/016,315 (retrievable from Pair), mailed Sep. 24, 2009.
Office Action issued in connection with co-pending U.S. Appl. No. 11/432,616, filed on May 12, 2006 (retrievable from PAIR), mailed on Apr. 16, 2009.
Office Action issued in connection with co-pending U.S. Appl. No. 12/016,315, filed on Jan. 18, 2008 (retrievable from PAIR), mailed on Apr. 2, 2009.
Office Action issued in connection with co-pending U.S. Appl. No. 12/016,315, filed on Jan. 18, 2008, mailed on Sep. 24, 2009.
Office Action issued in connection with co-pending U.S. Appl. No. 11/415,284, filed on May 2, 2006, mailed on Nov. 25, 2009.
Restriction Requirement Office Action received in connection with co-pending U.S. Appl. No. 11/738,889, filed on Apr. 23, 2007, mailed on May 26, 2010.
Notice of Allowance Office Action issued in connection with co-pending U.S. Appl. No. 11/432,616, filed on May 12, 2006, mailed on Mar. 25, 2010.
Notice of Allowance Office Action issued in connection with co-pending U.S. Appl. No. 12/016,315, filed on Jan. 1, 2008, mailed on Mar. 26, 2010.
Office Action issued in connection with co-pending U.S. Appl. No. 11/415,284, filed on May 2, 2006, mailed on Apr. 13, 2010.
Co-pending U.S. Appl. No. 12/752,048, "Blood Sample Holder for Spectroscopic Analysis", filed Mar. 31, 2010 (Available in PAIR).
Notice of Allowance received on the co-pending U.S. Appl. No. 11/432,616 filed on May 12, 2006, mailed on Jun. 14, 2010.

* cited by examiner

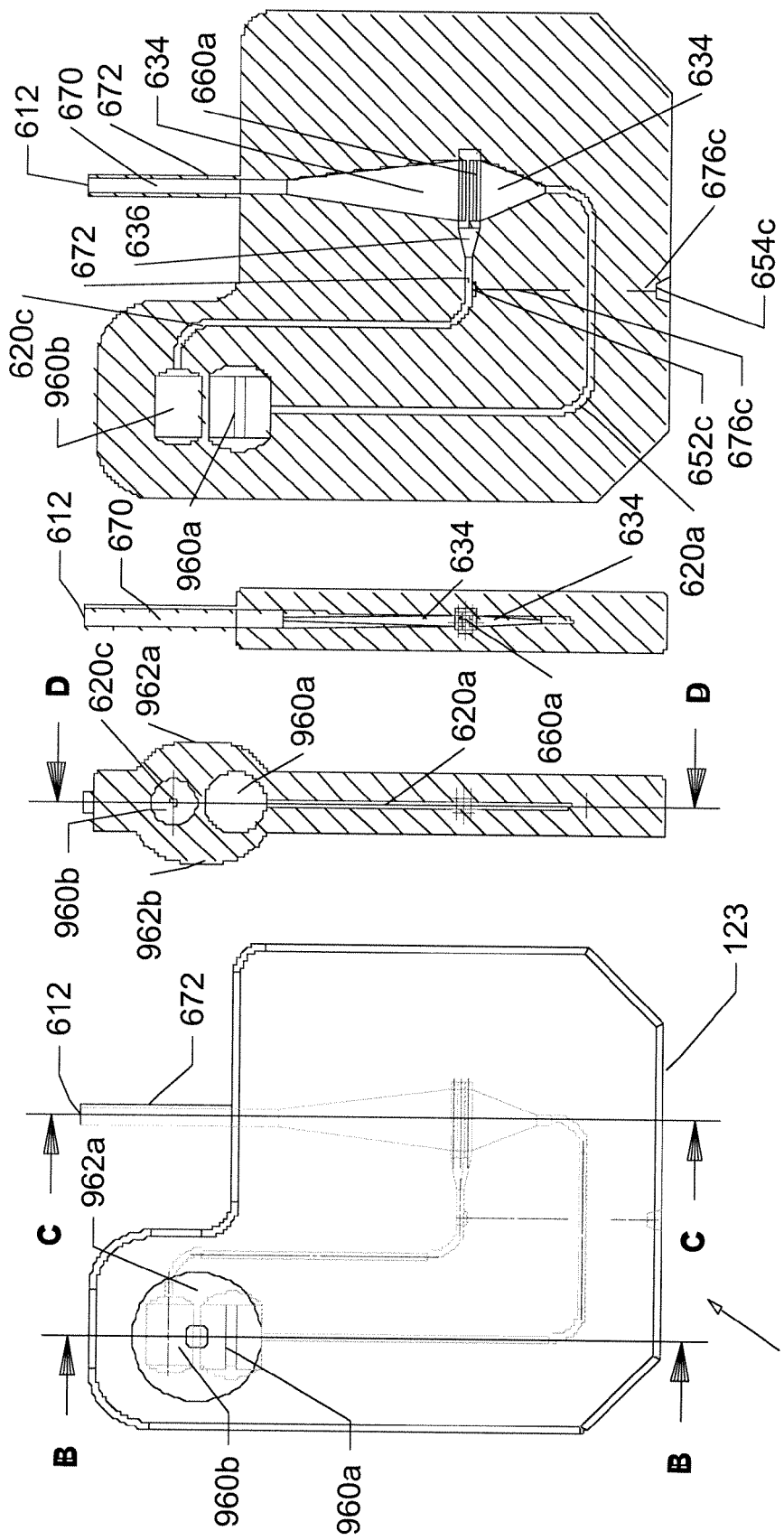

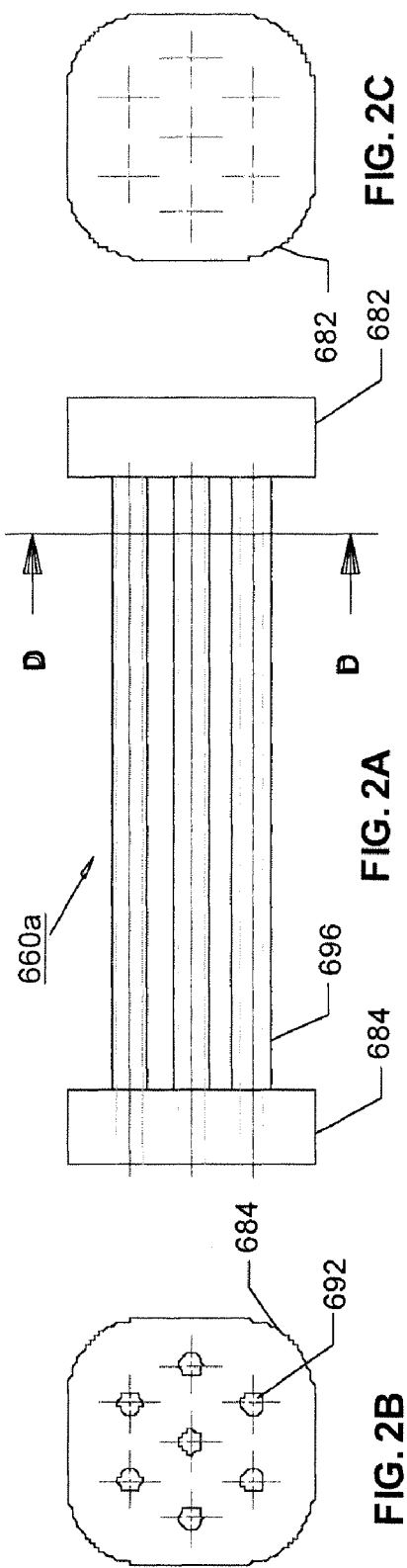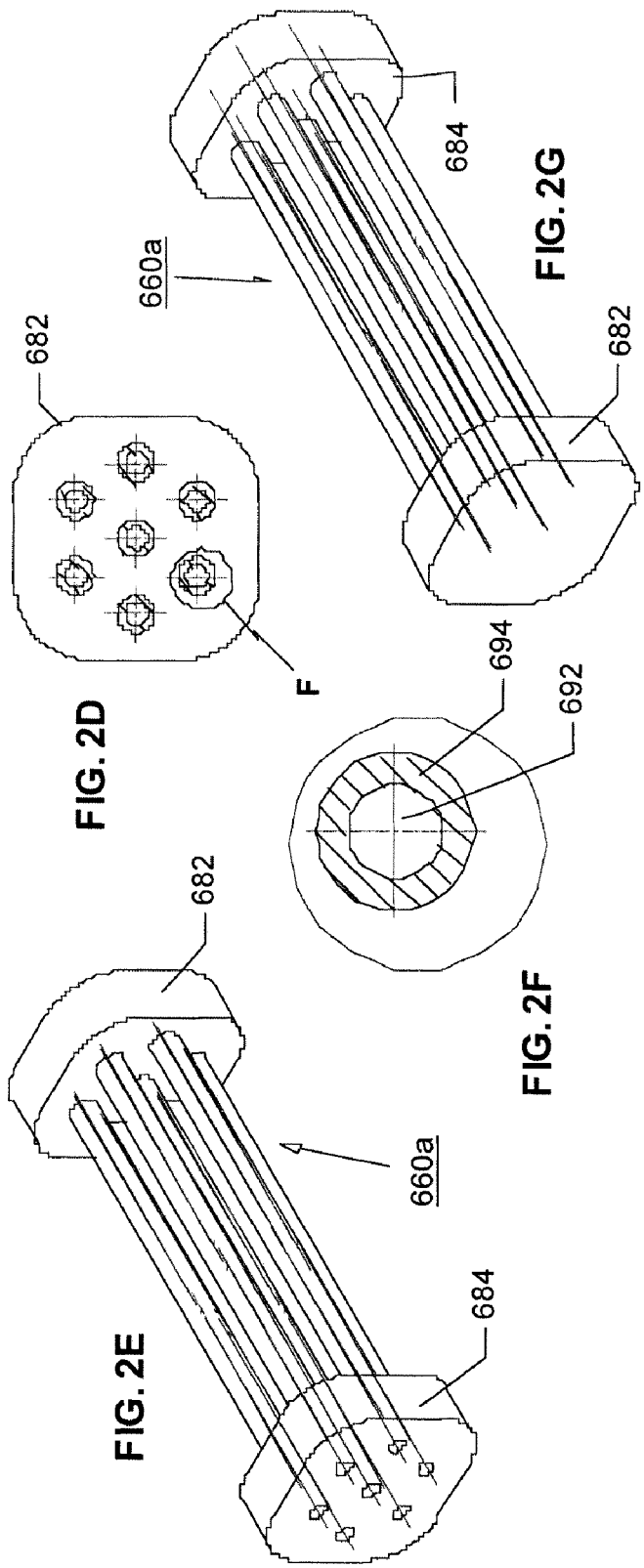

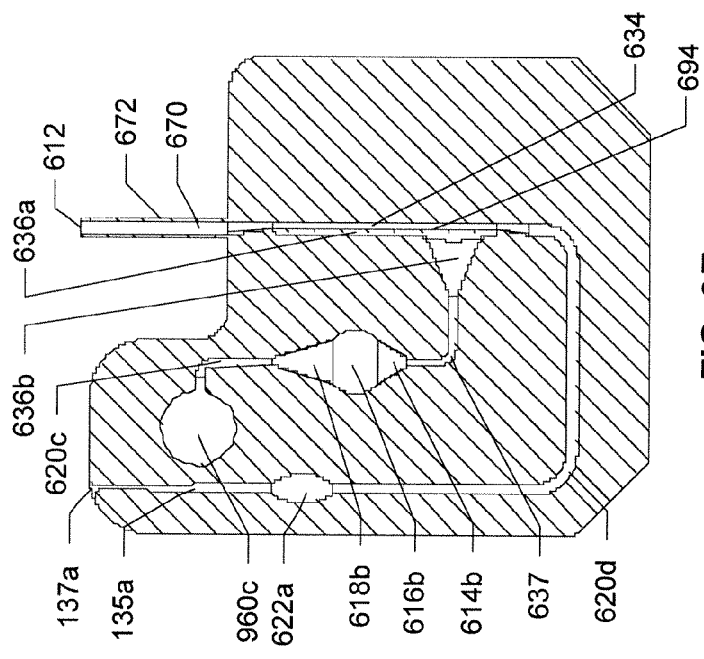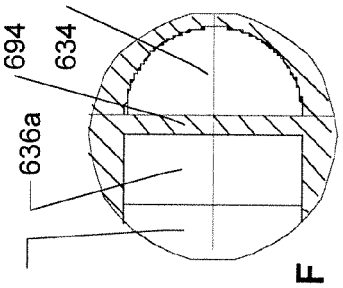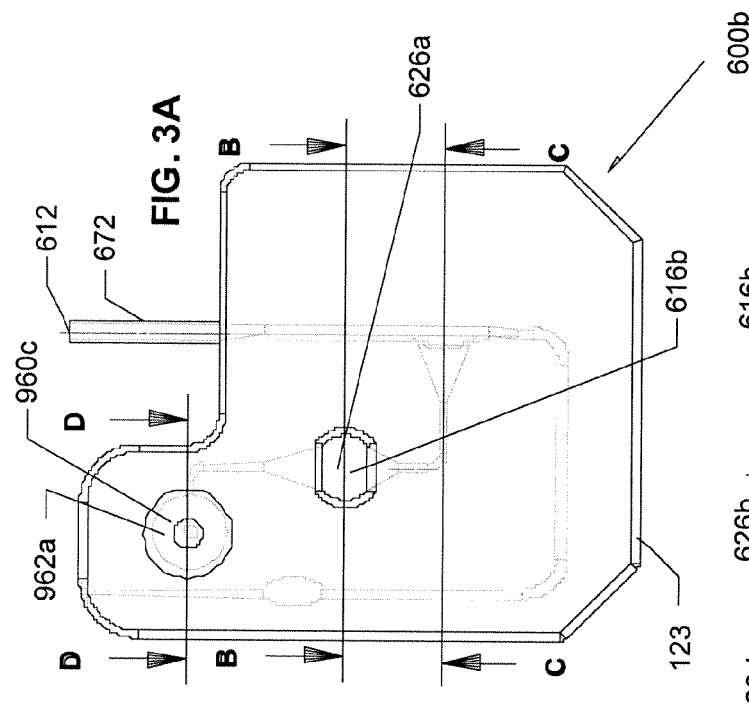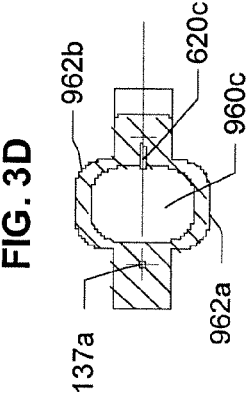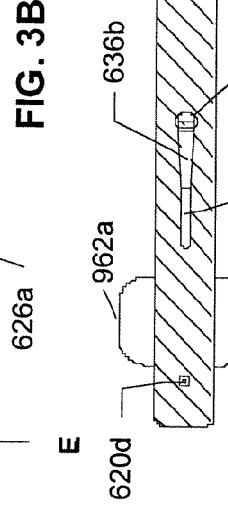

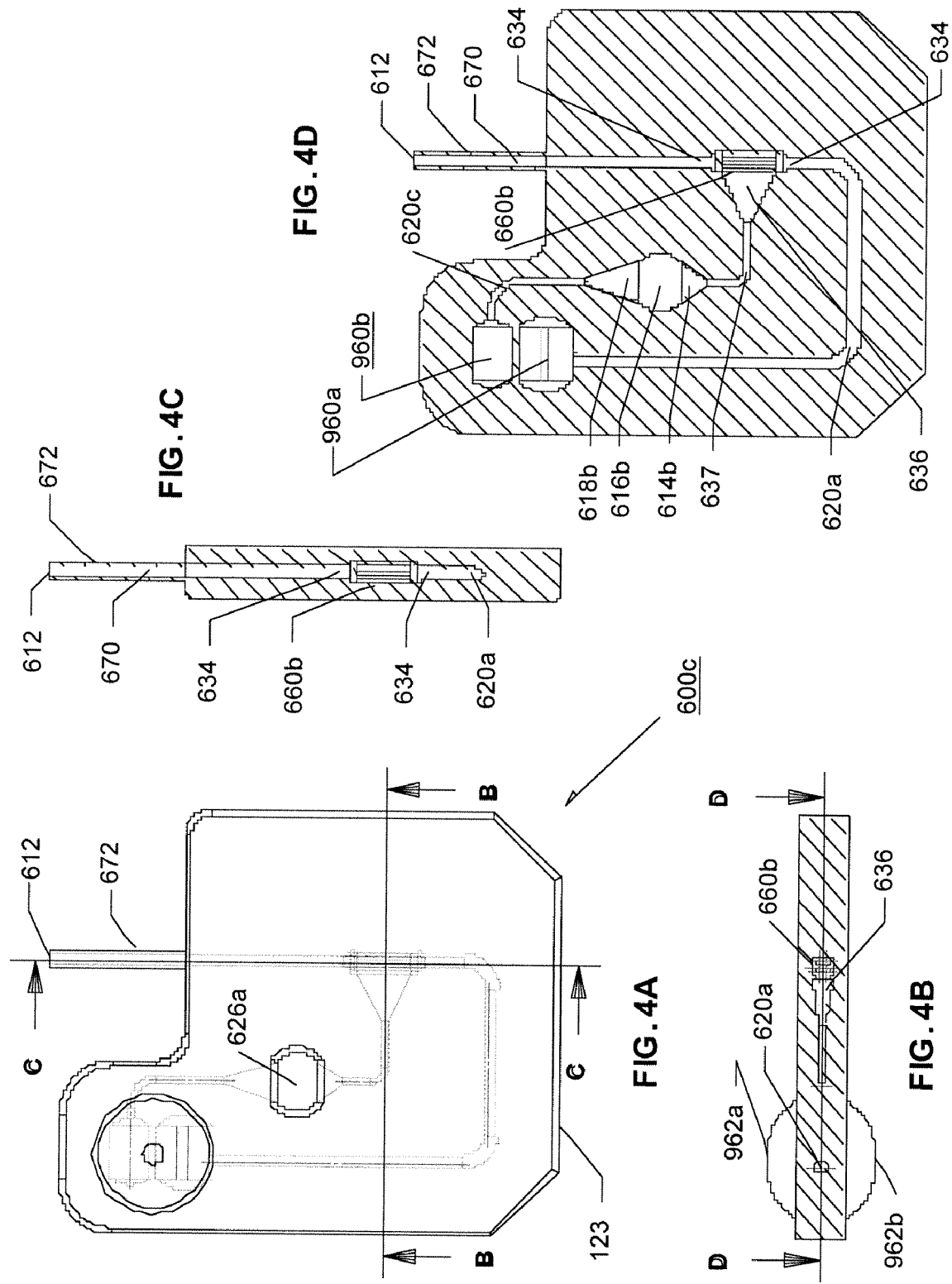

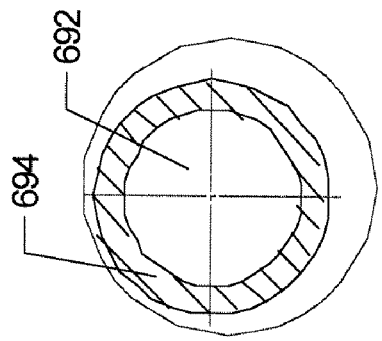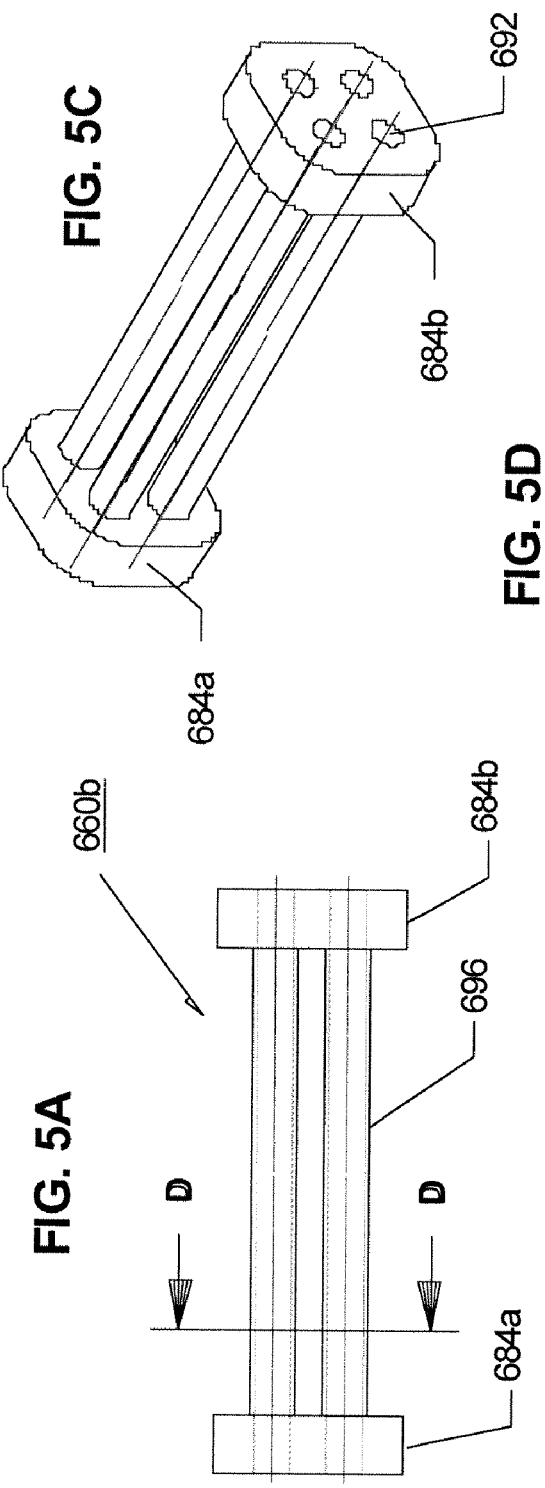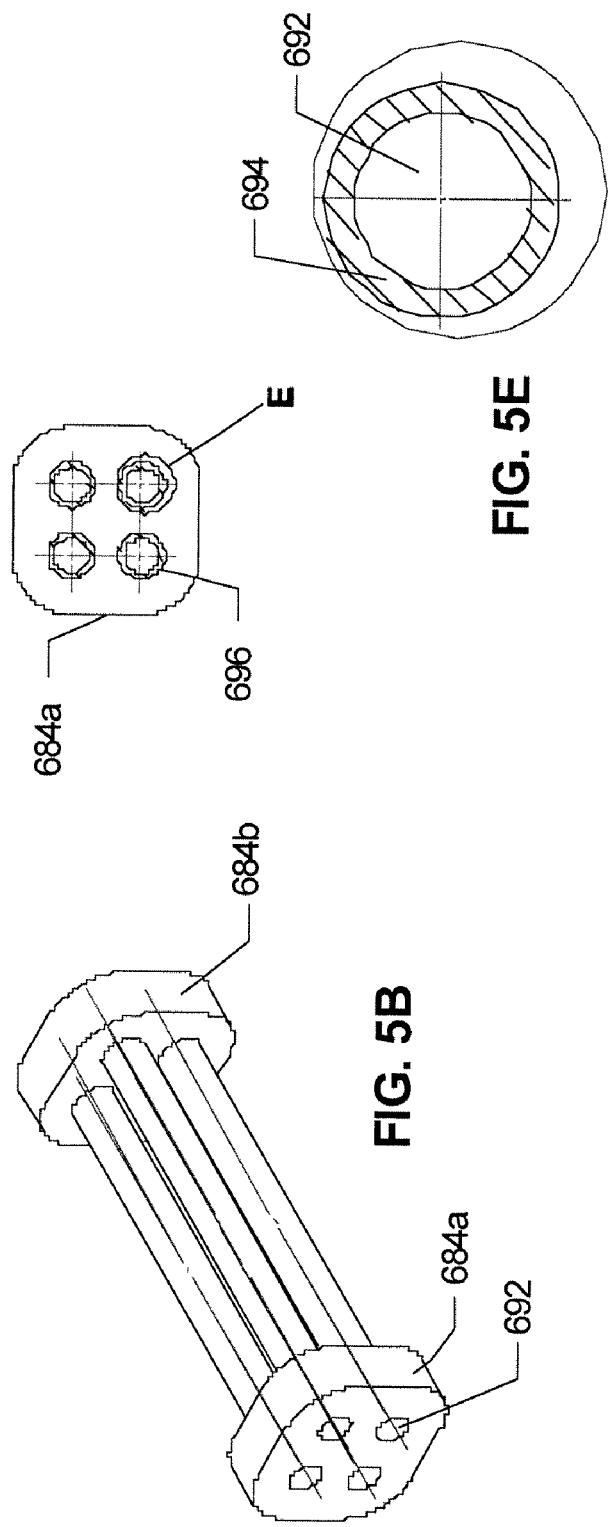

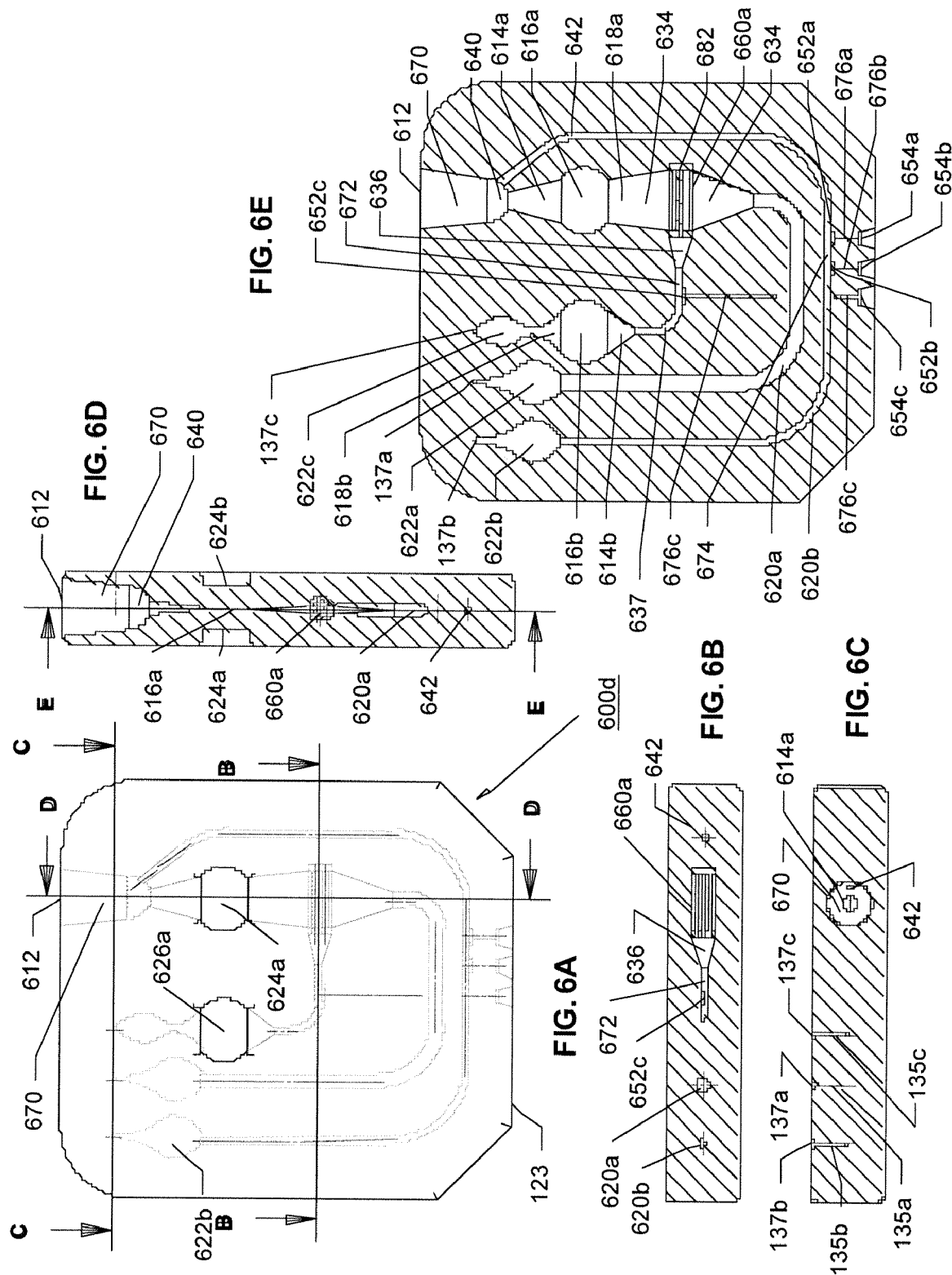

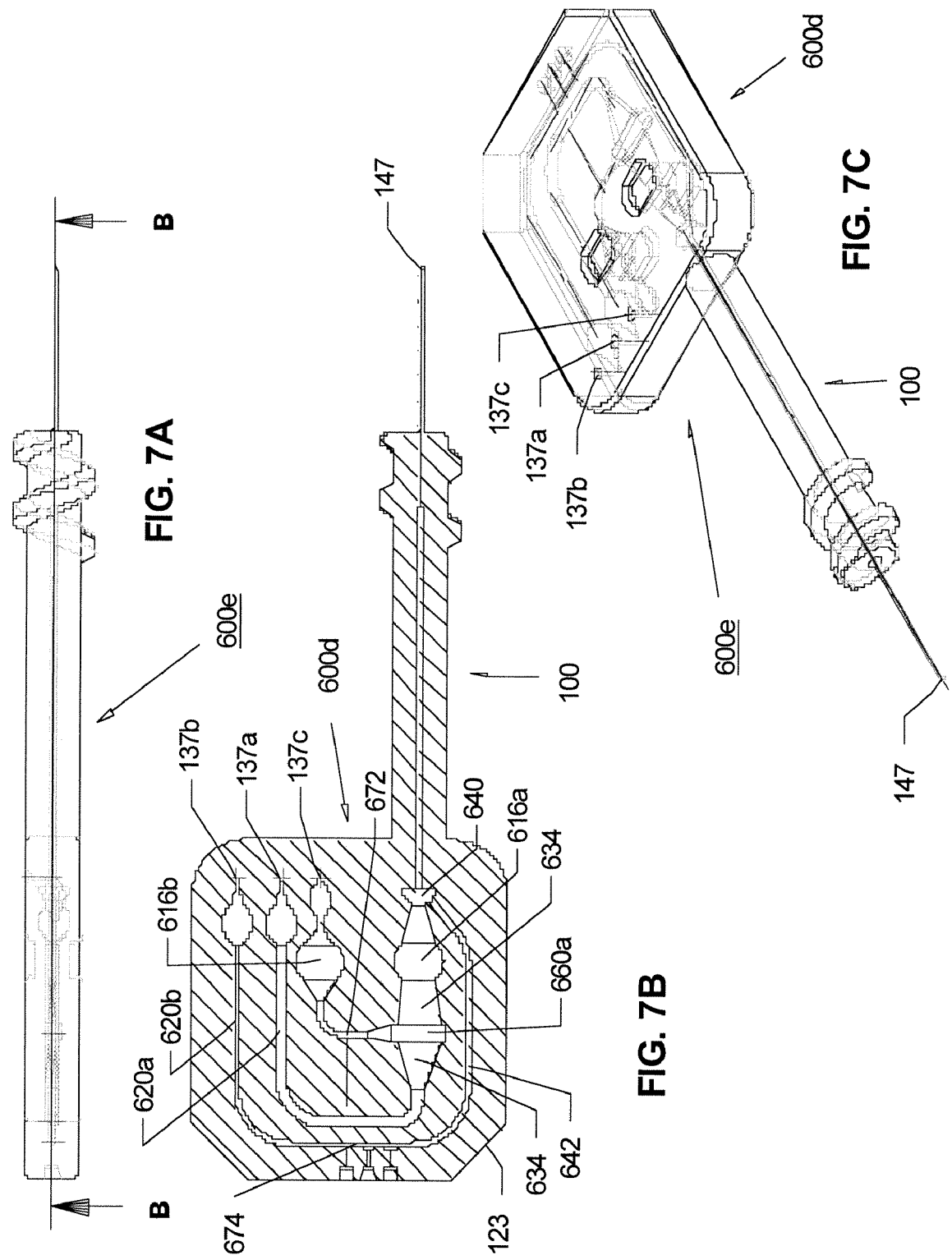

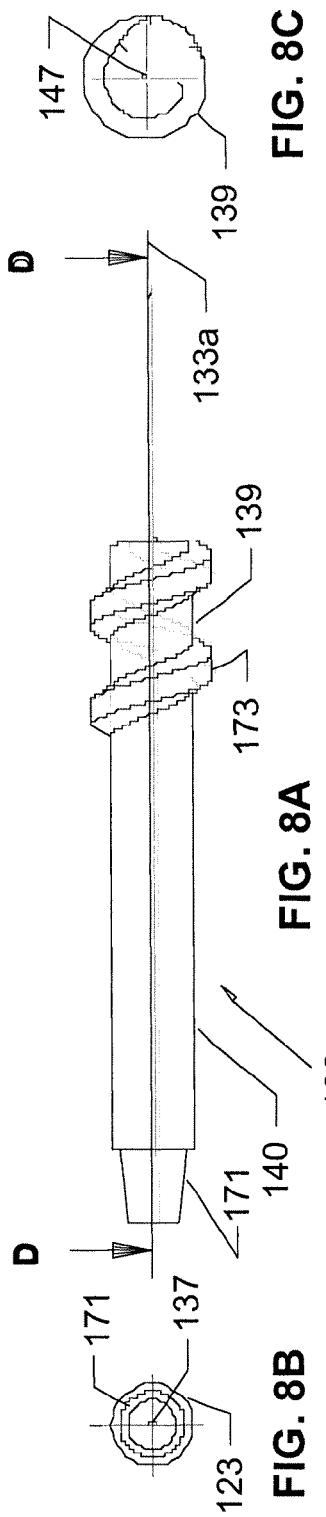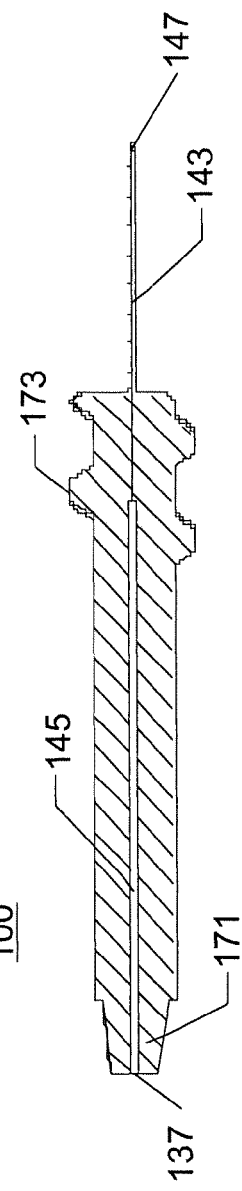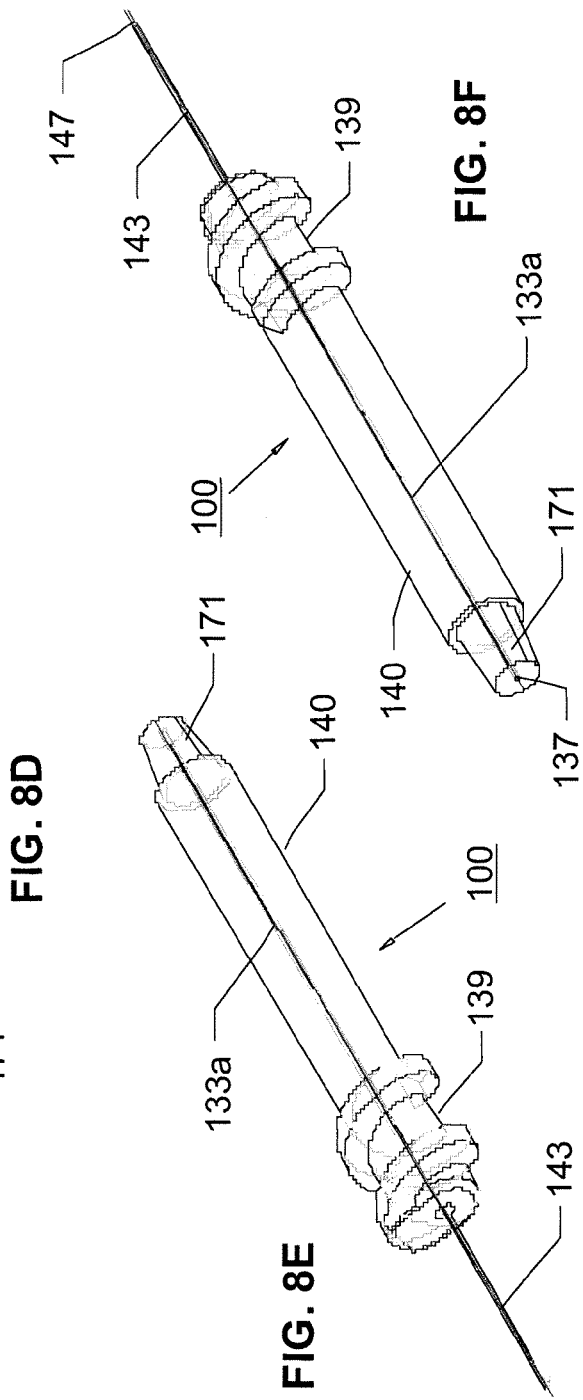

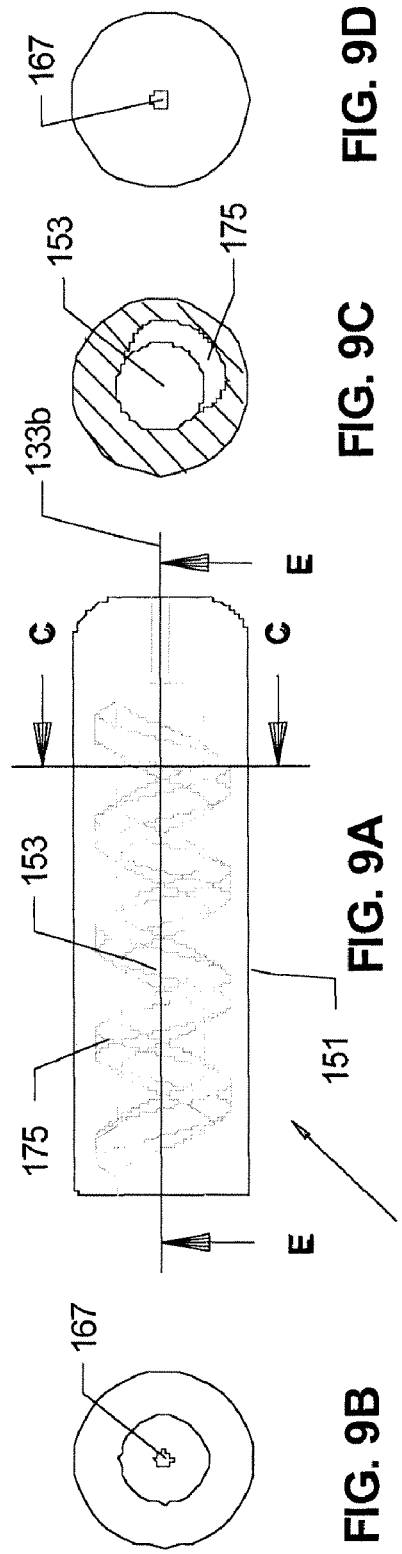

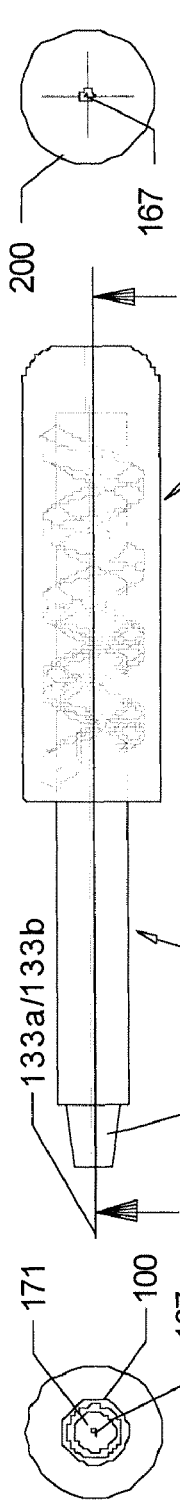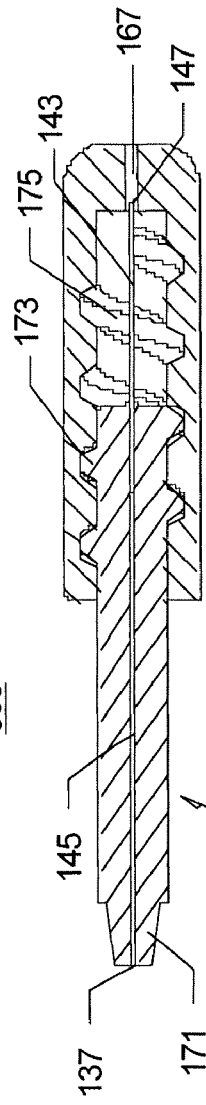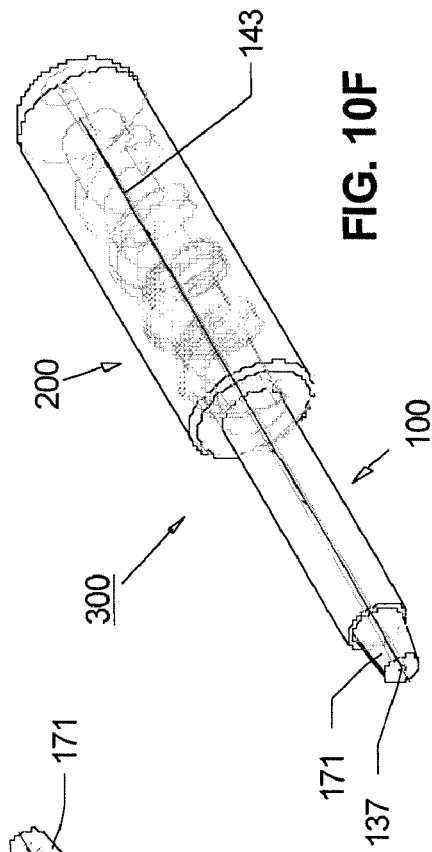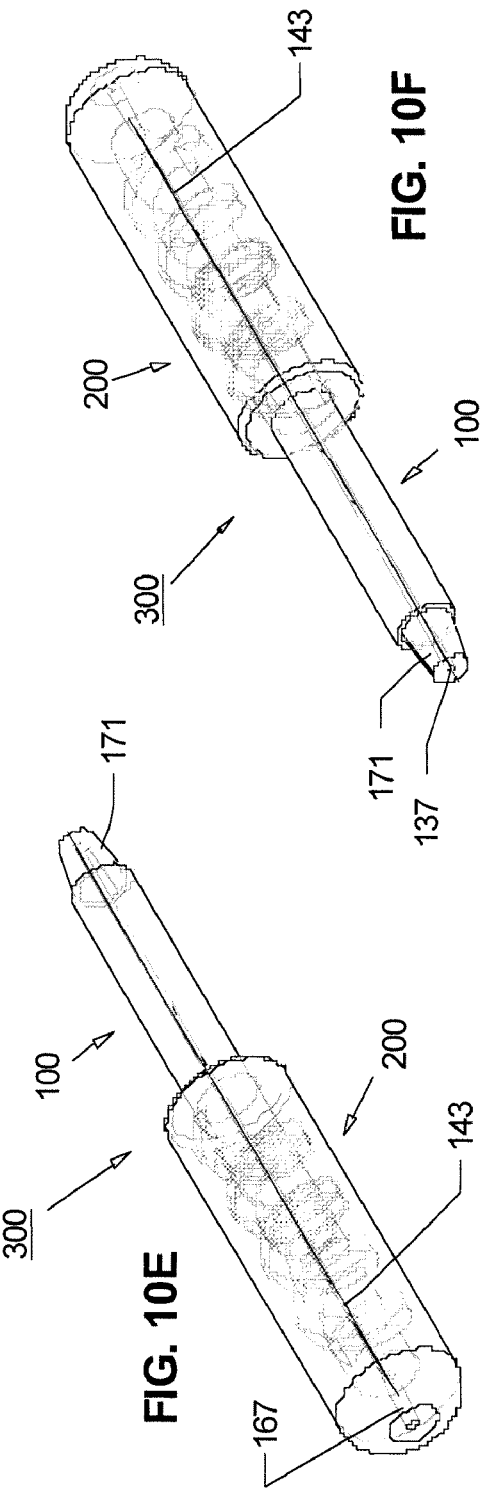

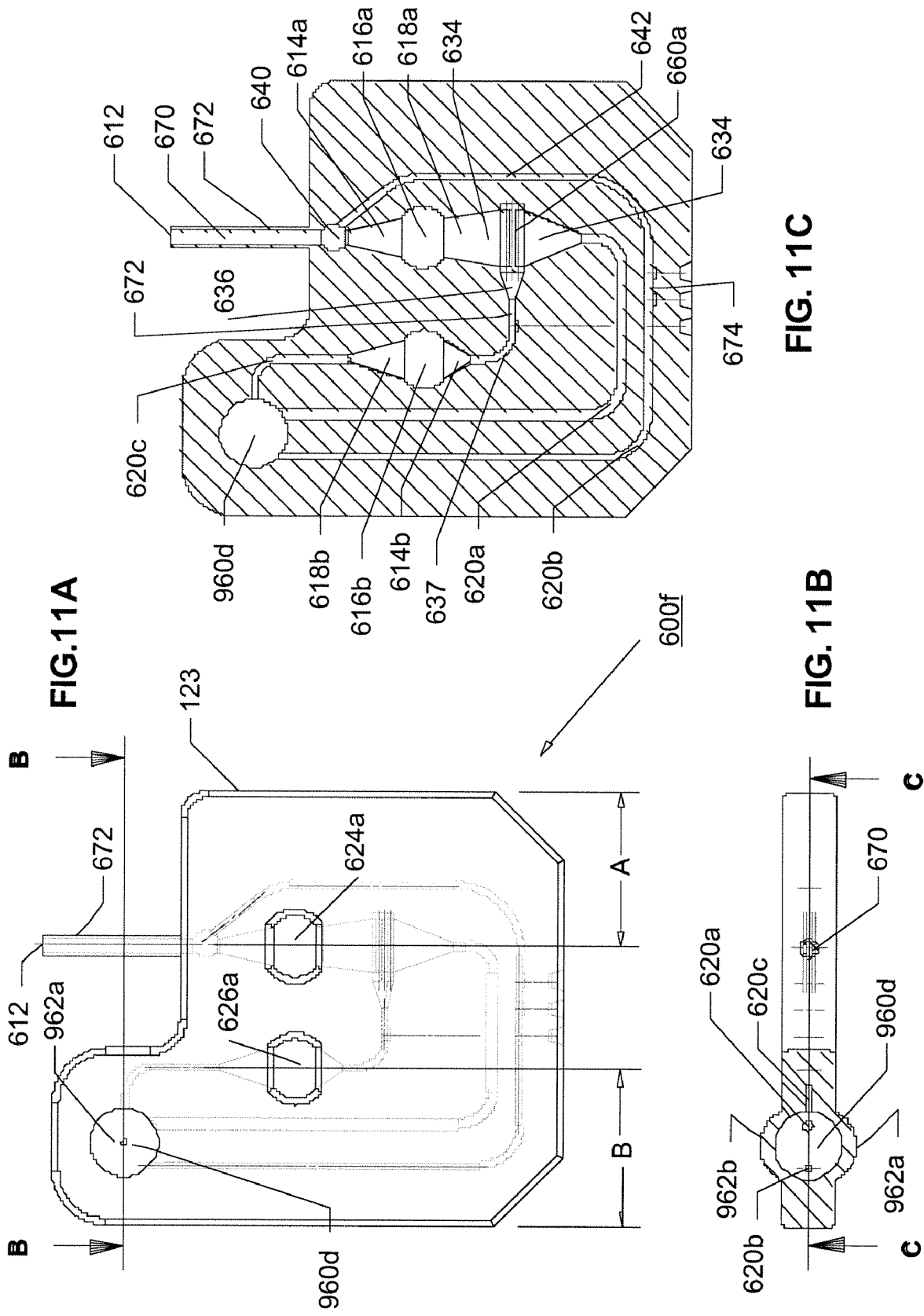

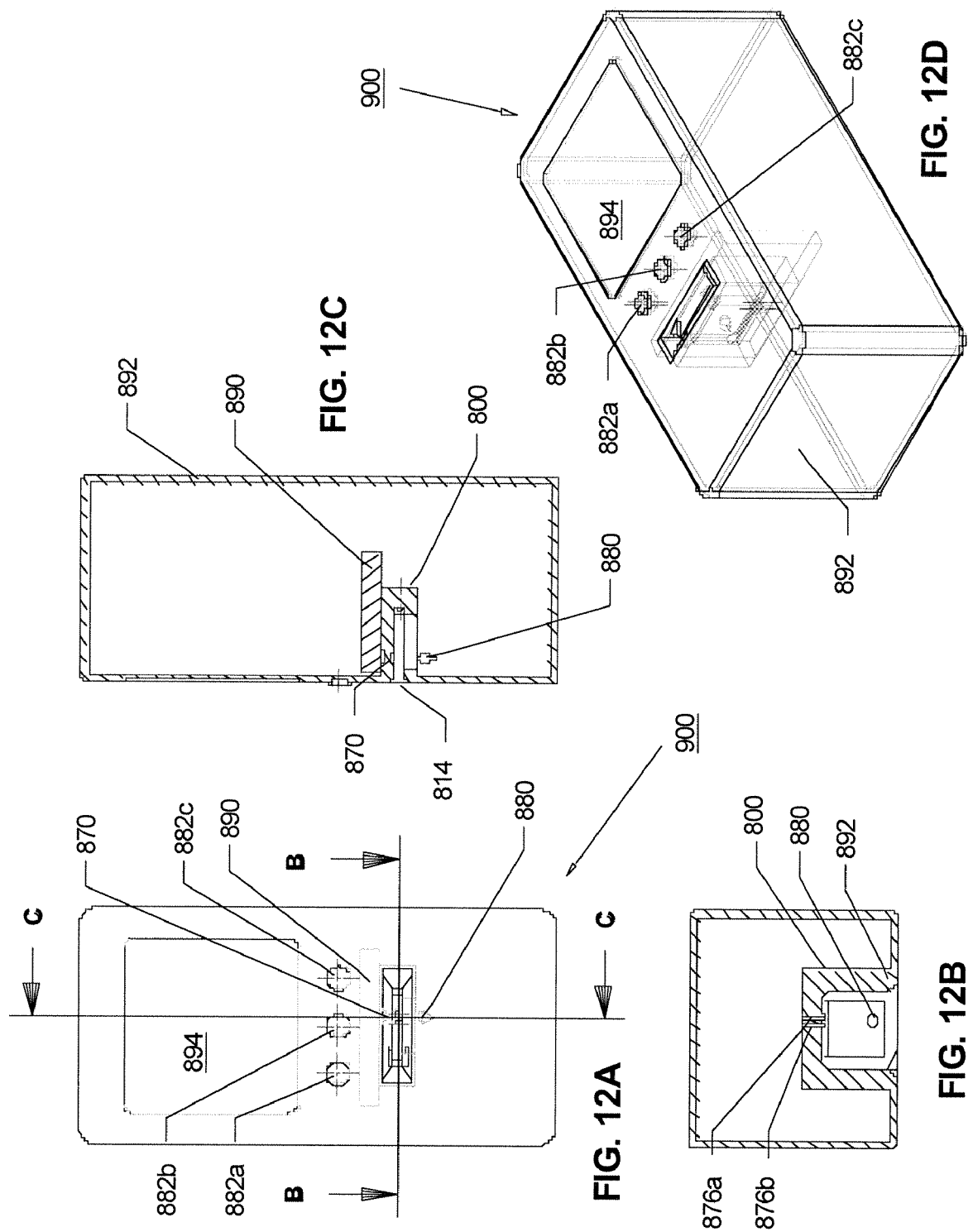

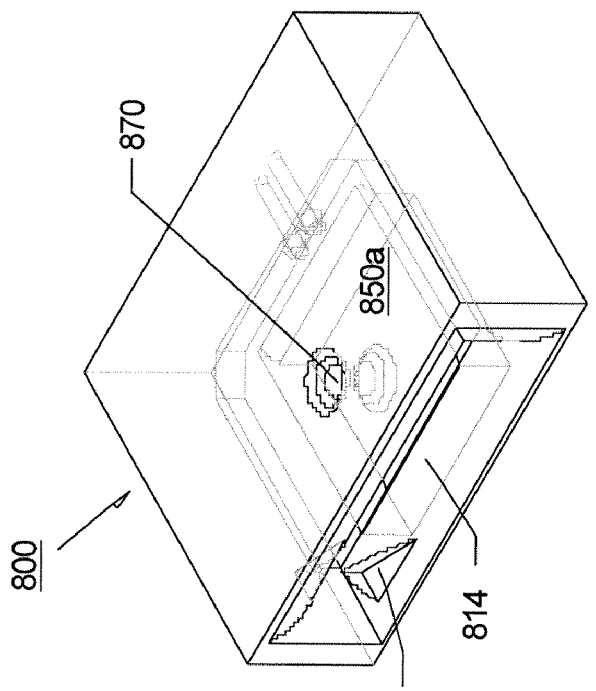
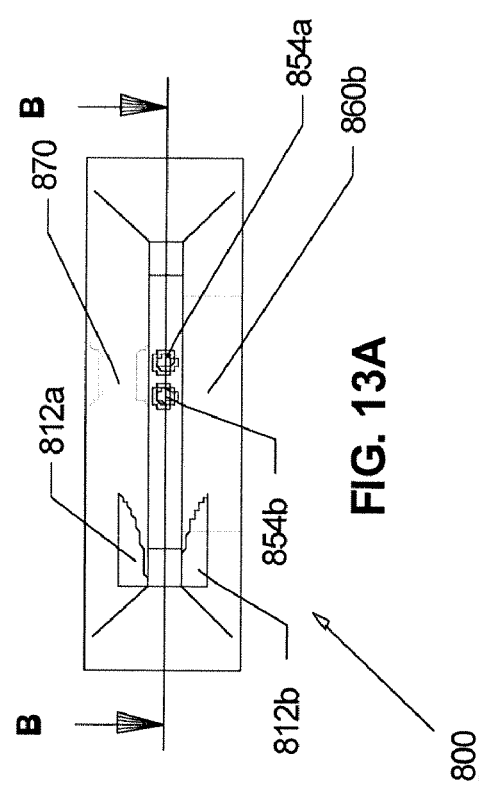
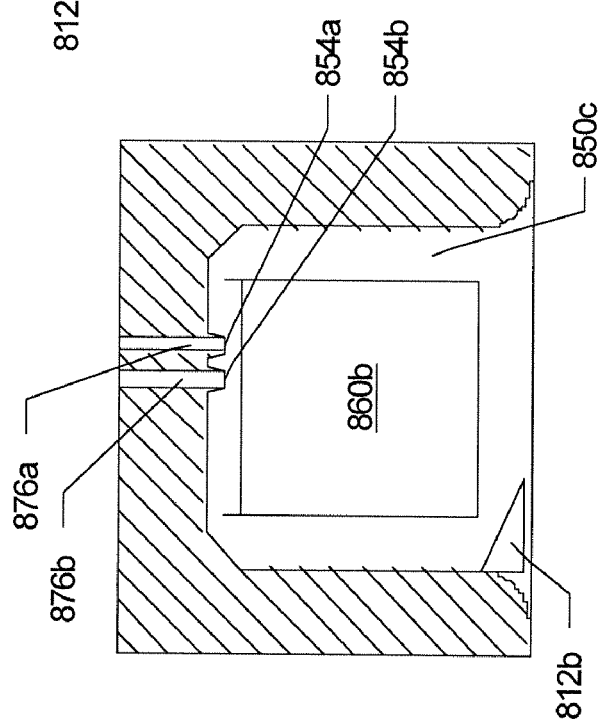
FIG. 13A
FIG. 13B
FIG. 13C

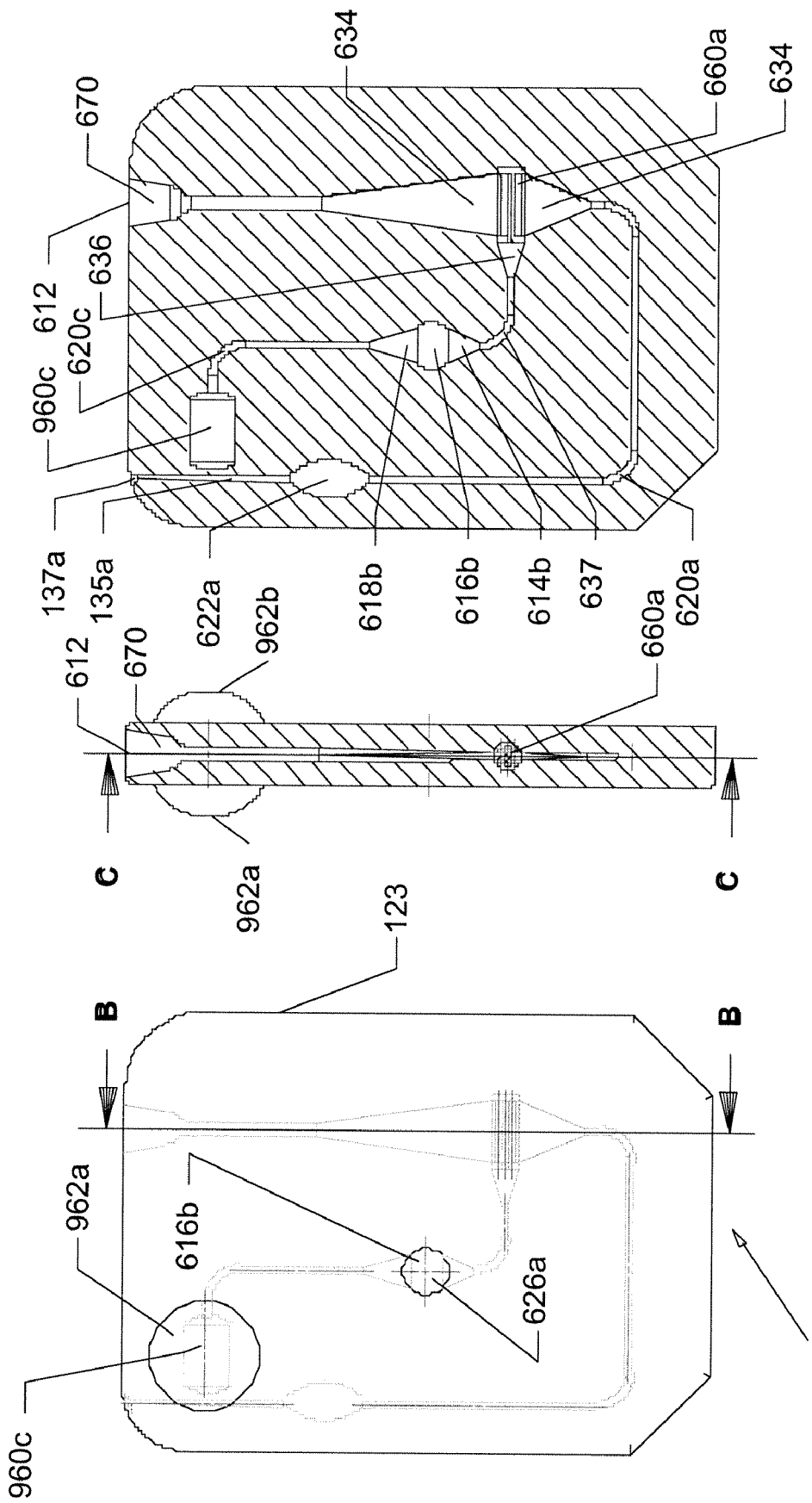

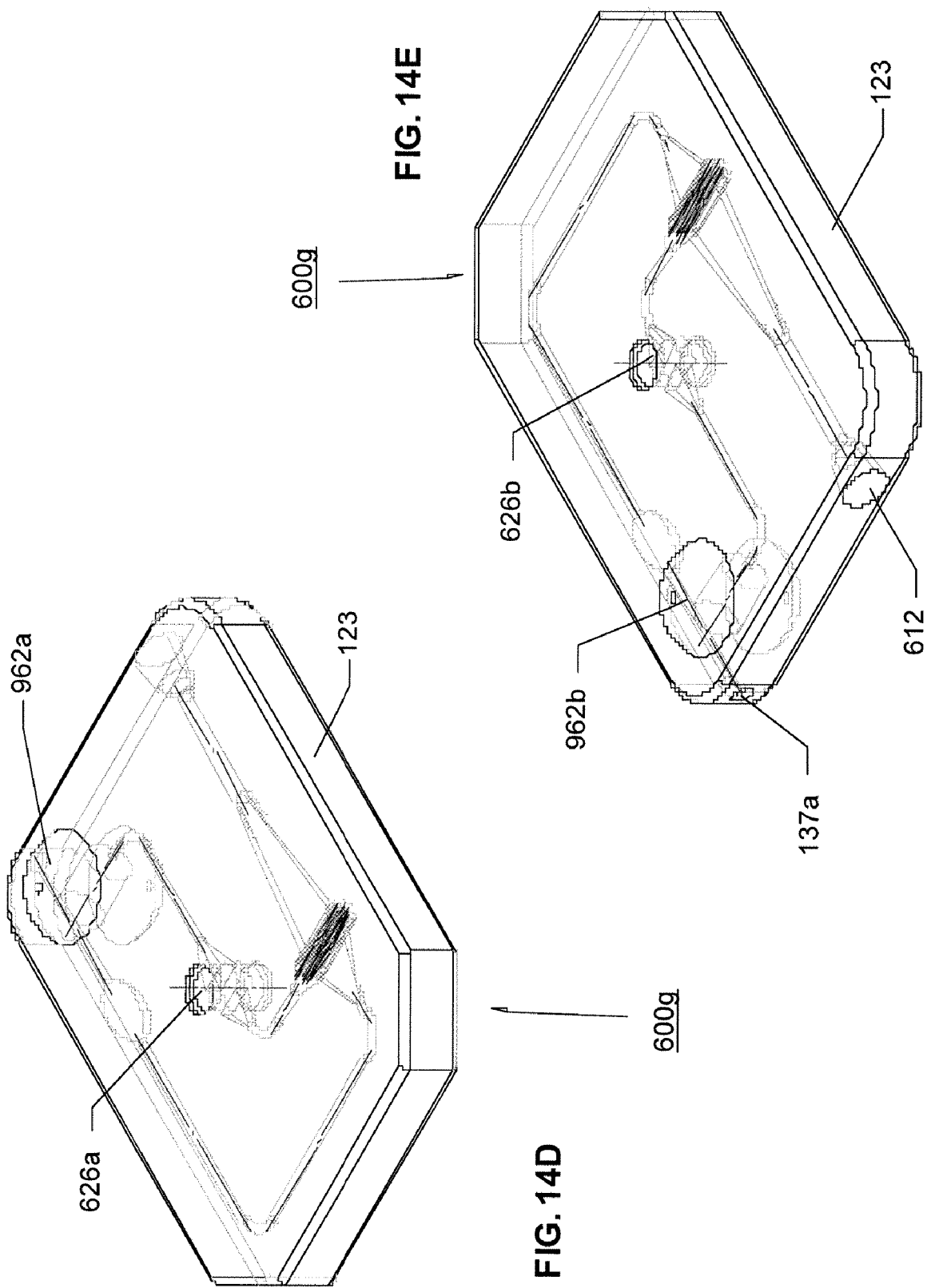

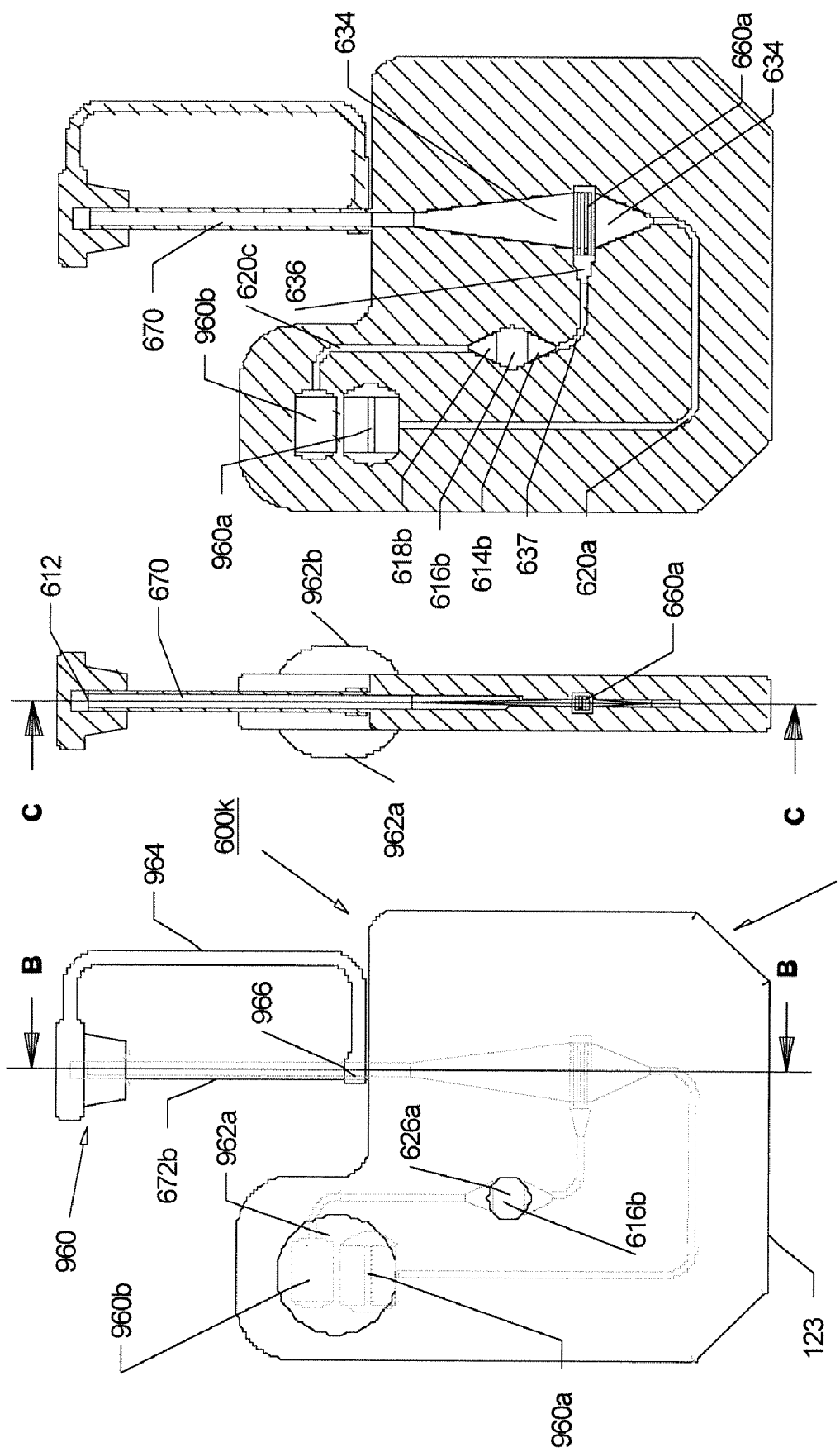

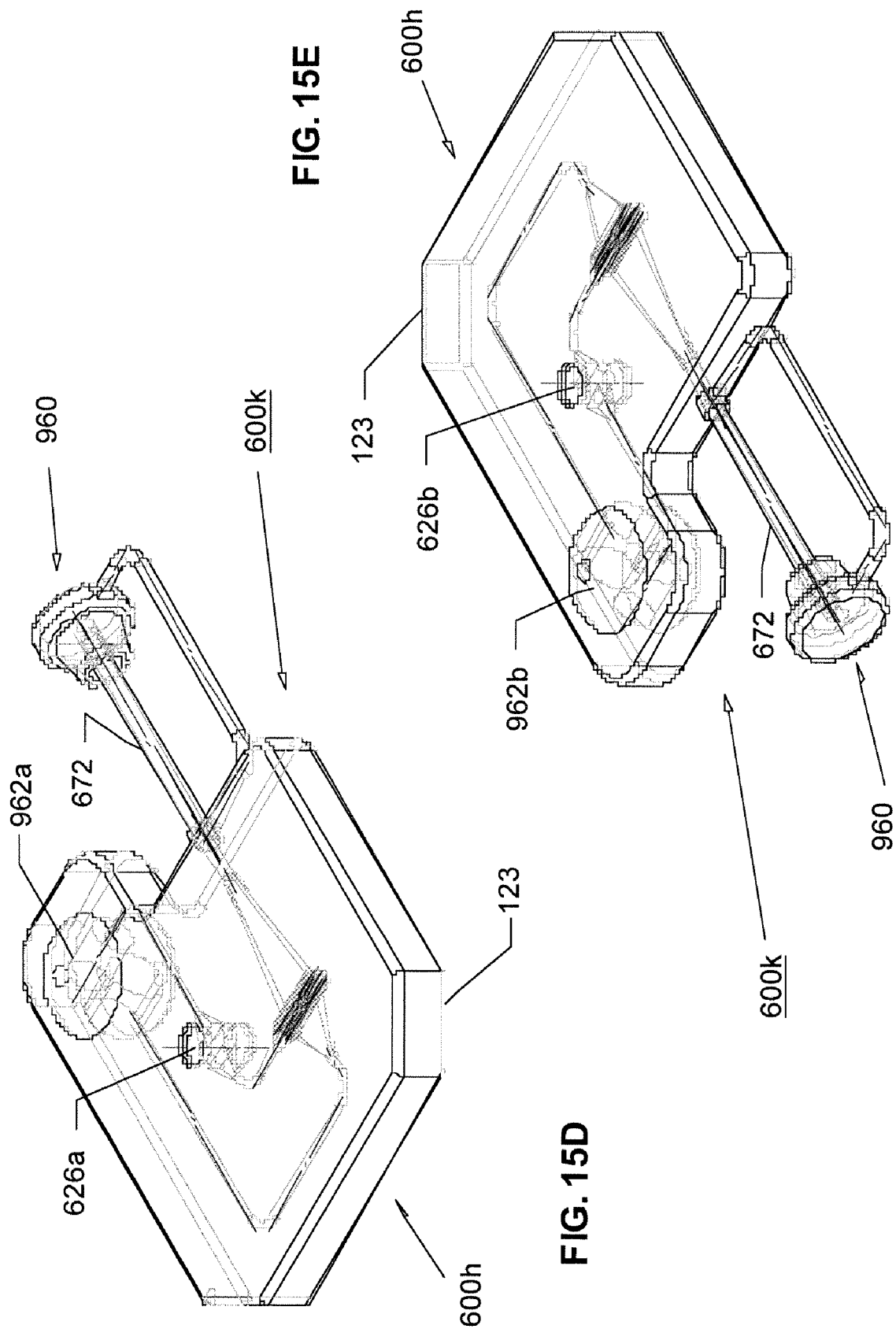

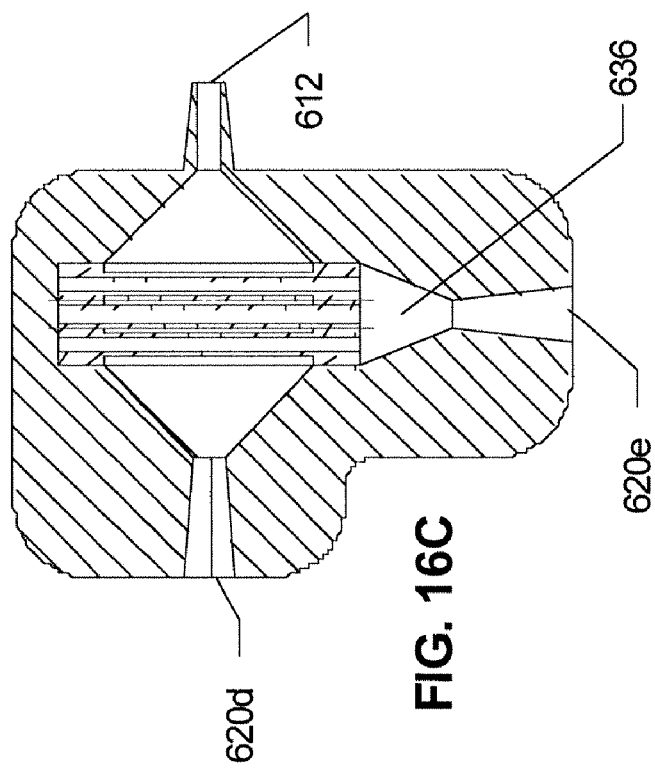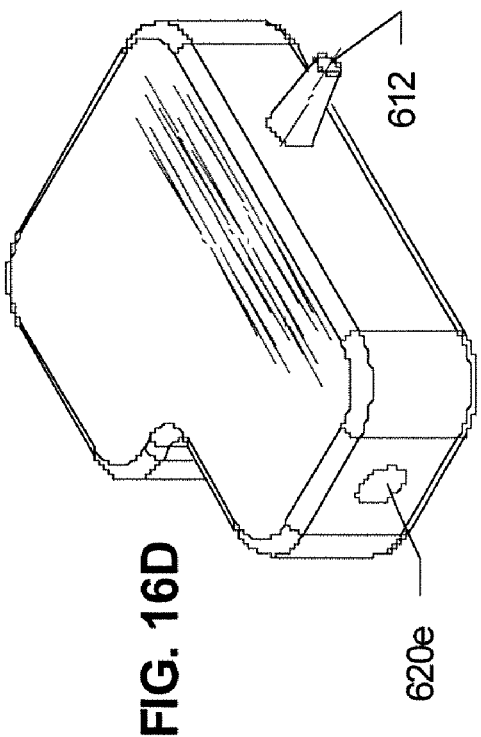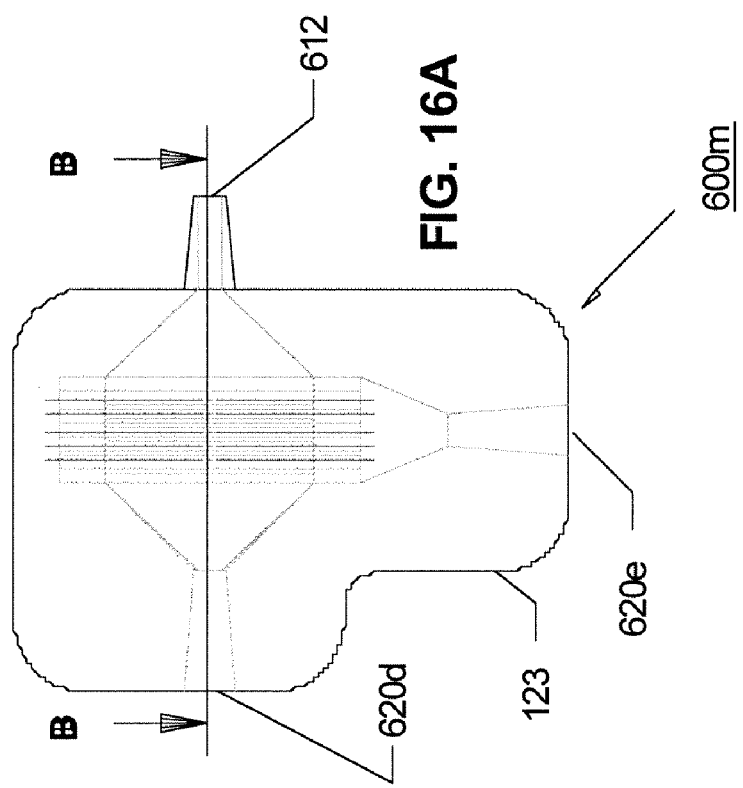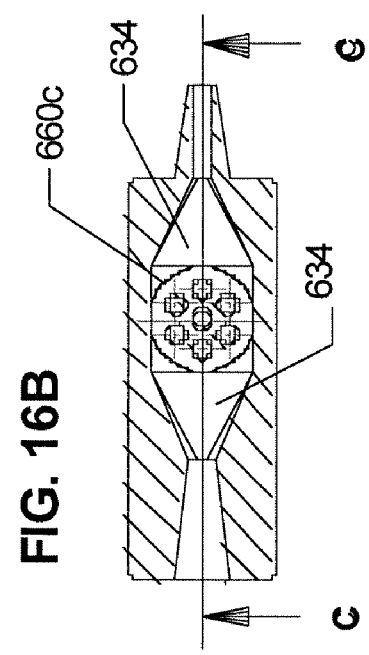

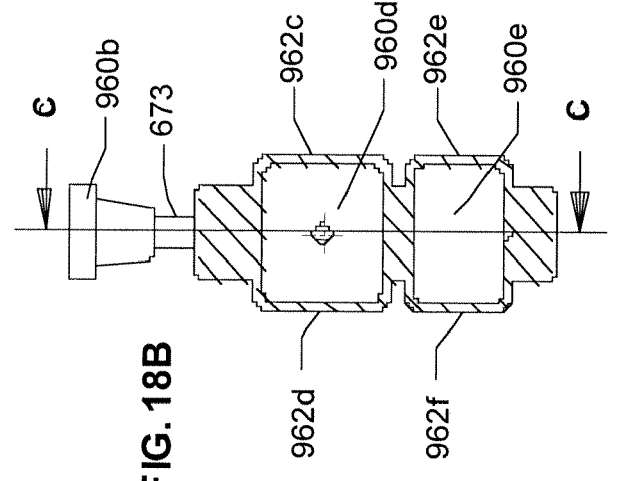
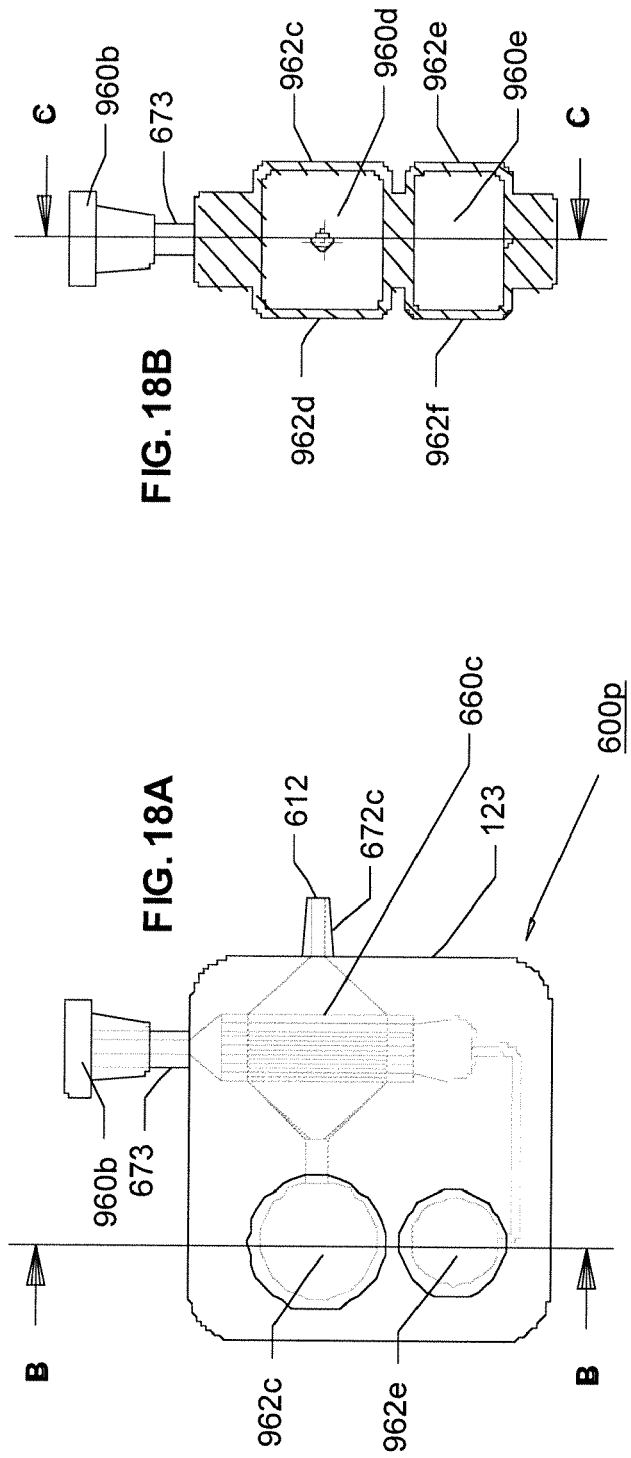
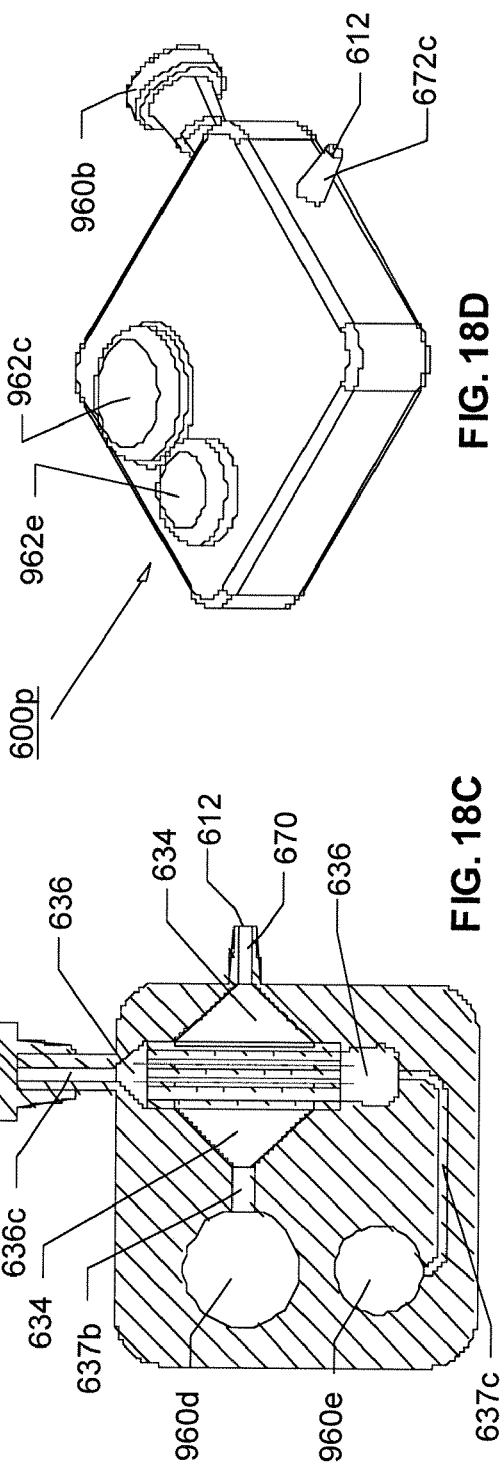

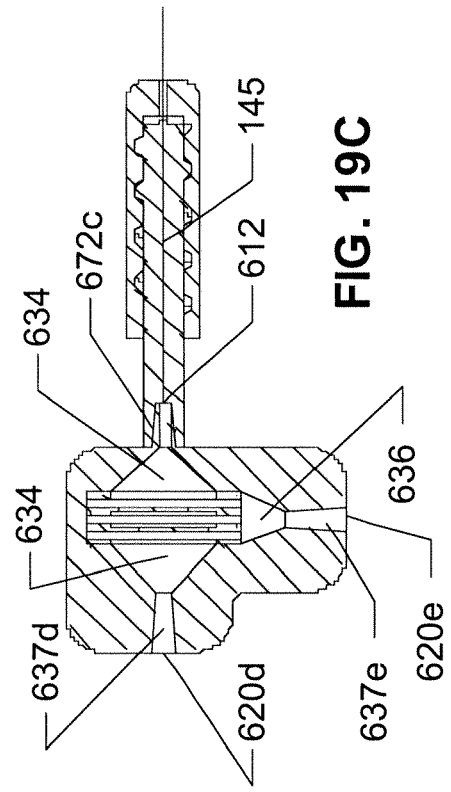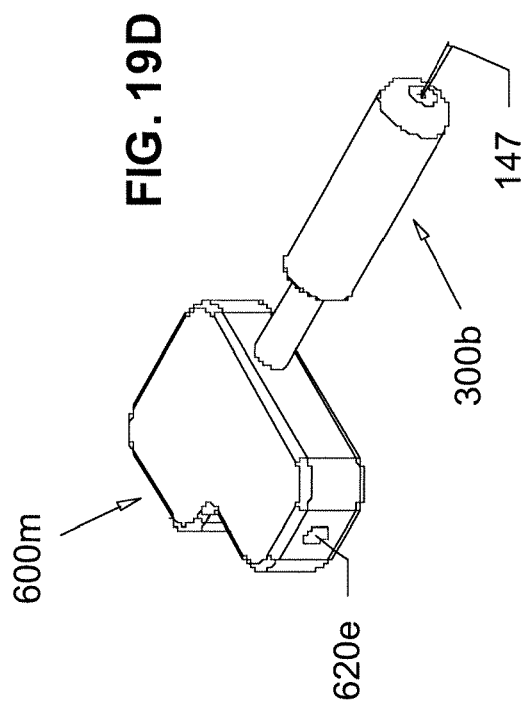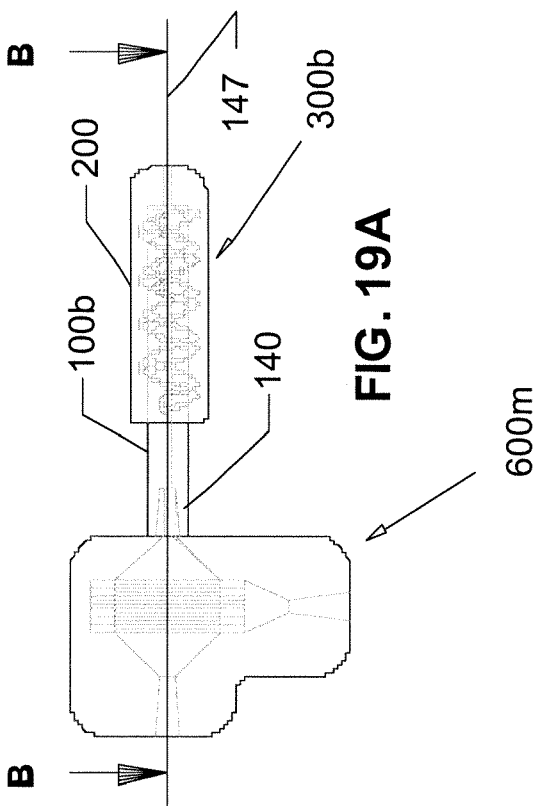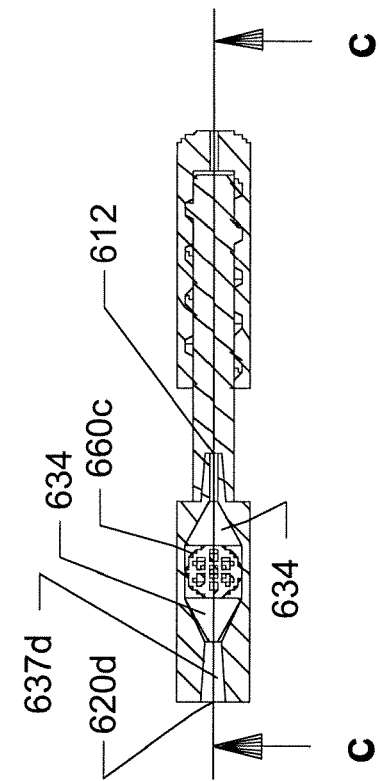

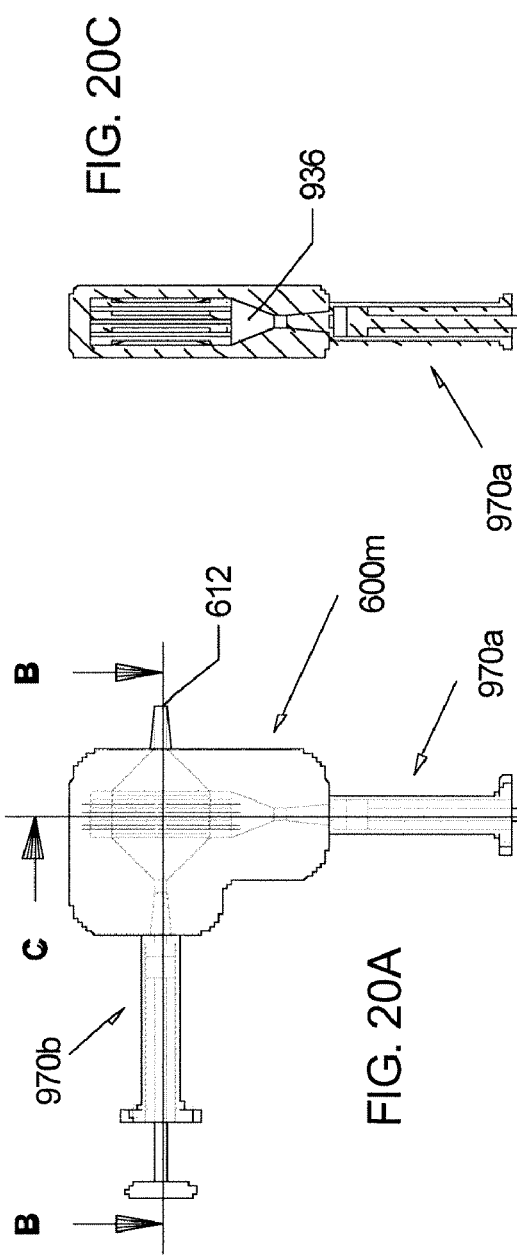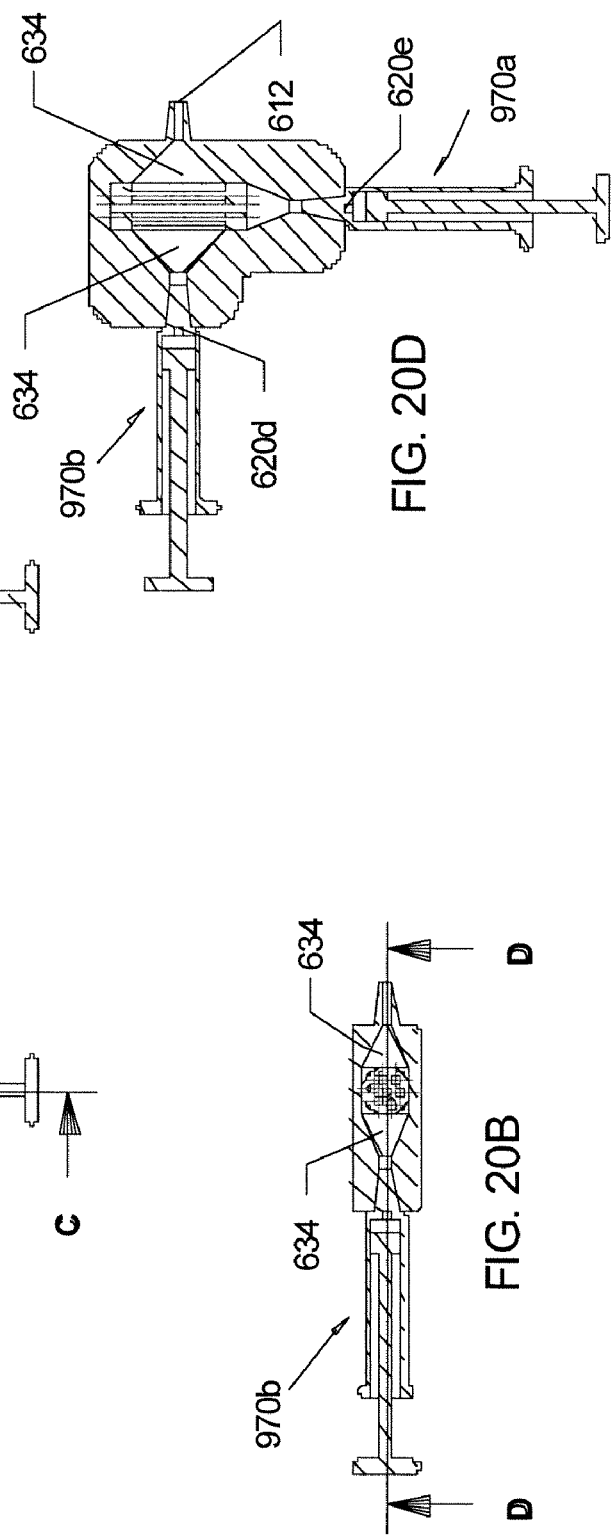
FIG. 20A
FIG. 20B
FIG. 20C
FIG. 20D

PLASMA EXTRACTION APPARATUS

RELATED APPLICATIONS

This application is a continuation-in-part of U.S. patent application Ser. No. 11/432,616, filed May 12, 2006, the entire content of which is hereby incorporated by reference.

FIELD OF THE INVENTION

The invention relates to an apparatus that rapidly extracts plasma from whole blood.

BACKGROUND OF THE INVENTION

Many medical diagnostic tests are performed in a medical laboratory, on serum and plasma. Serum is the yellow liquid obtained from whole blood (also referred to as blood) after the blood is allowed to clot, and the clot is removed by centrifugation; plasma is the yellow liquid obtained from blood by centrifugation of blood before the blood is allowed to clot, and the packed red cells are removed by centrifugation. Plasma is usually obtained by adding an anticoagulant like heparin to the blood, to prevent clotting.

Whole blood comprises the formed elements (i.e., the cellular components and the cell-derived components), and plasma; plasma is a natural component of whole blood. Red blood cells are the most abundant formed elements in blood, and platelets are examples of cell-derived components.

Spectroscopy or spectroscopic methods, with and without reagents added to the sample, are common methods used to measure analytes in serum and plasma. In spectroscopic measurements, the hemoglobin inside the red cells absorbs a very significant portion of the incident or illuminating electromagnetic radiation (EMR), and the red cells cause significant attenuation of the incident EMR due to scattering of EMR away from the photodetector. Therefore, when one is interested in the plasma concentration of an analyte, the serum or plasma is the preferred sample. As an example, bilirubin measurement by spectroscopy is accomplished much easier in serum and plasma than in whole blood. On the other hand, certain analytes can only be measured in blood because they only exist within the red cells, for example the various hemoglobin species.

Currently, not all diagnostic tests can be performed by spectroscopic methods, and the use of biosensors is another example of measurement techniques that can assist in expanding the menu of diagnostic tests. Because serum and plasma are less viscous that blood, serum or plasma may be preferred to blood when certain biosensors are employed.

Another reason for preferring serum and plasma over whole blood is the ability to detect hemolysis, turbidity, and elevated bilirubin in the serum and plasma, which cannot be detected in whole blood, and which affect the accuracy of many analyte measurements. Hemolysis is the release of hemoglobin and other red cell contents into the plasma or serum after rupture of red blood cells, and turbidity is the presence of light-scattering particles, for example, fat particles in the blood.

In point-of-care testing or near patient testing, the preferred sample is whole blood because the time and cost required for clotting and/or centrifugation is eliminated, and less blood is required. A drop of blood from a pin prick is the sample of choice for point-of-care testing or point-of-care measuring devices. However, if plasma or serum was as readily available, they would be preferred over whole blood for measurement of most analytes. Plasma is preferred over serum because the time required for clotting makes the turn-around time longer when serum is used for analysis.

Currently a centrifuge is necessary in order to obtain plasma from blood, and there is a need for a simpler and faster method of obtaining plasma, particularly for point-of-care testing.

SUMMARY OF THE INVENTION

According to an aspect of an embodiment of the invention there is provided a system for extracting plasma from blood received from a blood supply, the system comprising: a) a housing; b) an inlet opening in the housing for receiving the blood; c) a blood flow path in the housing beginning at the inlet opening and terminating at one of i) a blood flow path outlet and ii) a blood flow path compression chamber for facilitating a blood flow in the blood flow path; d) a filtration chamber within the housing for receiving the blood from the inlet opening, the filtration chamber comprising a membrane separating the blood flow path from a plasma compartment, wherein the blood flow path intersects with the filtration chamber at a fluid intersection; and e) a plasma flow path beginning at the plasma compartment and terminating at a manually operable plasma flow path compression chamber for pulling the plasma across the membrane from the blood flow path to the plasma compartment, wherein the plasma flow path compression chamber defines a cavity, at least a portion of the cavity being located within the housing.

According to an aspect of an embodiment of the invention there is provided a system for extracting plasma from blood, comprising: a) a housing; b) an inlet opening in the housing for receiving the blood; c) a blood flow path beginning at the inlet opening and terminating at a manually operable blood flow path compression chamber for facilitating a blood flow in the blood flow path, wherein the blood flow path compression chamber defines a cavity, at least a portion of the cavity being located within the housing; d) a filtration chamber within the housing for receiving the blood from the inlet opening, the filtration chamber comprising a membrane separating the blood flow path from a plasma compartment, wherein the blood flow path intersects with the filtration chamber at a fluid intersection; and e) a first plasma flow path beginning at the plasma compartment and terminating at one of a first plasma flow path outlet and a first plasma flow path compression chamber for drawing the plasma across the membrane, from the blood flow path to the plasma compartment.

In some embodiments of the present invention, the system comprises at least one of an optical chamber and a biosensor to facilitate analysis of at least one of blood and plasma.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 1A is a schematic drawing showing details of a top view of an apparatus 600a suitable for both extraction of plasma from a whole blood sample, and plasma analyte measurement according to a first embodiment of the invention;

FIG. 1B is a first cross-sectional view through the apparatus 600a shown in FIG. 1A along line B-B;

FIG. 1C is a second cross-sectional view through the apparatus 600a shown in FIG. 1A along line C-C;

FIG. 1D is a third cross-sectional view through the apparatus 600a shown in FIG. 1A and FIG. 1B along line D-D;

FIG. 2A is schematic drawing showing details of the hollow fiber filter bundle 660a shown in apparatus 600a, which is shown collectively in FIGS. 1A-1D;

FIG. 2B is the left side view of the hollow fiber filter bundle 660a shown in FIG. 2A;

FIG. 2C is the right side view of the hollow fiber filter bundle 660a shown in FIG. 2A;

FIG. 2D is a cross-sectional view through the hollow fiber filter bundle 660a shown in FIG. 2A along line D-D;

FIG. 2E is a perspective view of the hollow fiber filter bundle 660a shown in FIG. 2A;

FIG. 2F is a detailed view of the detail F shown in FIG. 2D;

FIG. 2G is an alternative perspective view of the hollow fiber filter bundle 660a shown in FIG. 2A;

FIG. 3A is a schematic drawing showing details of a top view of an apparatus 600b suitable for both extraction of plasma from a whole blood sample, and plasma analyte measurement according to a second embodiment of the invention;

FIG. 3B is a first cross-sectional view through the apparatus 600b shown in FIG. 3A along line B-B;

FIG. 3C is a second cross-sectional view through the apparatus 600b shown in FIG. 3A along line C-C;

FIG. 3D is a third cross-sectional view through the apparatus 600b shown in FIG. 3A along line D-D;

FIG. 3E is a fourth cross-sectional view through the apparatus 600b shown in FIG. 3A and FIG. 3B along line E-E;

FIG. 3F is a detailed view of the detail F shown in FIG. 3C;

FIG. 4A is a schematic drawing showing details of a top view of an apparatus 600c suitable for both extraction of plasma from a whole blood sample, and plasma analyte measurement according to a third embodiment of the invention;

FIG. 4B is a first cross-sectional view through the apparatus 600c shown in FIG. 4A along line B-B;

FIG. 4C is a second cross-sectional view through the apparatus 600c shown in FIG. 4A along line C-C;

FIG. 4D is a third cross-sectional view through the apparatus 600c shown in FIG. 4A and FIG. 4B along line D-D;

FIG. 5A is schematic drawing showing details of a hollow fiber filter bundle 660b shown in apparatus 600c, which is shown collectively in FIGS. 4A-4D;

FIG. 5B is a perspective view of the hollow fiber filter bundle 660b shown in FIG. 5A;

FIG. 5C is an alternative perspective view of the hollow fiber filter bundle 660b shown in FIG. 5A;

FIG. 5D is a cross-sectional view through the hollow fiber filter bundle 660b shown in FIG. 5A along line D-D;

FIG. 5E is a detailed view of detail E shown in FIG. 5D;

FIG. 6A is a schematic drawing showing details of the top view of an apparatus 600d suitable for both extraction of plasma from a whole blood sample, and plasma and whole blood analyte measurement according to a fourth embodiment of the invention;

FIG. 6B is a first cross-sectional view through the apparatus 600d shown in FIG. 6A along line B-B;

FIG. 6C is a second cross-sectional view through the apparatus 600d shown in FIG. 6A along line C-C;

FIG. 6D is a third cross-sectional view through the apparatus 600d shown in FIG. 6A along line D-D;

FIG. 6E is a fourth cross-sectional view through the apparatus 600d shown in FIG. 6A and FIG. 6D along line E-E;

FIG. 7A is a schematic drawing showing details of the top view of an apparatus 600e suitable for both extraction of plasma from a whole blood sample, and plasma and whole blood analyte measurement according to a fifth embodiment of the invention;

FIG. 7B is a cross-sectional view through the apparatus 600e shown in FIG. 7A along line B-B;

FIG. 7C is a perspective view of the apparatus 600e shown in FIG. 7A;

FIG. 8A is a schematic drawing showing details of a top view of a hollow needle 100 that can be used with the apparatus 600d shown collectively in FIGS. 6A-6E, resulting in an apparatus similar to the apparatus 600e shown collectively in FIGS. 7A-C;

FIG. 8B is a left side view of the hollow needle 100 shown in FIG. 8A;

FIG. 8C is a right side view of the hollow needle 100 shown in FIG. 8A;

FIG. 8D is a cross-sectional view through the hollow needle 100 shown in FIG. 8A along line D-D;

FIG. 8E is a perspective view of the hollow needle 100 shown in FIG. 8A;

FIG. 8F is an alternative perspective view of the hollow needle 100 shown in FIG. 8A;

FIG. 9A is a schematic drawing showing details of a top view of a barrel 200 for a hollow needle assembly 300 shown collectively in FIGS. 10A-10F, for sheathing and unsheathing the needle 100 shown collectively in FIGS. 8A-8F;

FIG. 9B is a left side view of the barrel 200 shown in FIG. 9A;

FIG. 9C is a first cross-sectional view through the barrel 200 shown in FIG. 9A along line C-C;

FIG. 9D is a right side view of the barrel 200 shown in FIG. 9A;

FIG. 9E is a second cross-sectional view through the barrel 200 shown in FIG. 9A along line E-E;

FIG. 9F is a perspective view of the barrel 200 shown in FIG. 9A;

FIG. 10A is a schematic drawing showing details of a top view of a hollow needle assembly 300 of the needle 100 (shown collectively in FIGS. 8A-8F) and the barrel 200 (shown collectively in FIGS. 9A-9F), with the needle retracted into the barrel;

FIG. 10B is a left side view of the hollow needle assembly 300 shown in FIG. 10A;

FIG. 10C is a right side view of the hollow needle assembly 300 shown in FIG. 10A;

FIG. 10D is a cross-sectional view through the hollow needle assembly 300 shown in FIG. 10A along line D-D;

FIG. 10E is a perspective view of the hollow needle assembly 300 shown in FIG. 10A;

FIG. 10F is an alternative perspective view of the hollow needle assembly 300 shown in FIG. 10A;

FIG. 11A is a schematic drawing showing details of the top view of an apparatus 600f suitable for both extraction of plasma from a whole blood sample, and plasma and whole blood analyte measurement according to a sixth embodiment of the invention;

FIG. 11B is a first cross-sectional view through the apparatus 600f shown in FIG. 11A along line B-B;

FIG. 11C is a second cross-sectional view through the apparatus 600f shown in FIG. 11A and FIG. 11B along line C-C;

FIG. 12A is a schematic drawing showing details of a front view of a meter 900 that can be used with some embodiments of the whole blood and plasma apparatus;

FIG. 12B is a first cross-sectional view through the meter 900 shown in FIG. 12A along line B-B;

FIG. 12C is a second cross-sectional view through the meter 900 shown in FIG. 12A along line C-C;

FIG. 12D is a perspective view of the meter 900 shown in FIG. 12A;

FIG. 13A is a schematic drawing showing details of a front view of a meter slot 800 from a meter 900 shown collectively in FIGS. 12A-12D;

FIG. 13B is a cross-sectional view through the meter slot 800 shown in FIG. 13A along line B-B;

FIG. 13C is a perspective view of the meter slot 800 shown in FIG. 13A;

FIG. 14A is a schematic drawing showing details of the top view of an apparatus 600g suitable for both extraction of plasma from a whole blood sample, and plasma analyte measurement according to a seventh embodiment of the invention;

FIG. 14B is a first cross-sectional view through the apparatus 600g shown in FIG. 14A along line B-B;

FIG. 14C is a second cross-sectional view through the apparatus 600g shown in FIG. 14A and FIG. 14B along line C-C;

FIG. 14D is a perspective view of the apparatus 600g shown in FIG. 14A;

FIG. 14E is an alternative perspective view of the apparatus 600g shown in FIG. 14A;

FIG. 15A is a schematic drawing showing details of the top view of a combined apparatus (600h) and cap (960) 600k, suitable for both extraction of plasma from a whole blood sample, and plasma measurement according to a eight embodiment of the invention;

FIG. 15B is a first cross-sectional view through the combined apparatus and cap 600k shown in FIG. 15A along line B-B;

FIG. 15C is a second cross-sectional view through the combined apparatus and cap 600k shown in FIG. 15A and FIG. 15B along line C-C;

FIG. 15D is a perspective view of the combined apparatus and cap 600k shown in FIG. 15A;

FIG. 15E is an alternative perspective view of the combined apparatus and cap 600k shown in FIG. 15A.

FIG. 16A is a schematic drawing showing details of the top view of an apparatus 600m suitable for extraction of plasma from whole blood, according to a ninth embodiment of the invention;

FIG. 16B is a first cross-sectional view through the apparatus 600m shown in FIG. 16A along line B-B;

FIG. 16C is a second cross-sectional view through the apparatus 600m shown in FIG. 16A and FIG. 16B along line C-C;

FIG. 16D is a perspective view of the apparatus 600m shown in FIG. 16A;

FIG. 18A is a schematic drawing showing details of the top view of an apparatus 600p suitable for extraction of plasma from whole blood, according to an eleventh embodiment of the invention;

FIG. 18B is a first cross-sectional view through the apparatus 600m shown in FIG. 18A along line B-B;

FIG. 18C is a second cross-sectional view through the apparatus 600m shown in FIG. 18A and FIG. 18B along line C-C;

FIG. 18D is a perspective view of the apparatus 600p shown in FIG. 18A;

FIG. 19A is a schematic drawing showing details of the top view of an apparatus 600m (with a hollow needle assembly 300b attached) suitable for extraction of plasma from whole blood, according to the ninth embodiment of the invention;

FIG. 19B is a first cross-sectional view through the apparatus 600m (and the hollow needle assembly 300b) shown in FIG. 19A along line B-B;

FIG. 19C is a second cross-sectional view through the apparatus 600m (and the hollow needle assembly 300b) shown in FIG. 19A and FIG. 19B along line C-C;

FIG. 19D is a perspective view of the apparatus 600m (and the hollow needle assembly 300b) shown in FIG. 19A;

FIG. 20A is a schematic drawing showing details of the top view of an apparatus 600m (with two syringes 970a and 970b attached) suitable for extraction of plasma from whole blood, according to the ninth embodiment of the invention;

FIG. 20B is a first cross-sectional view through the apparatus 600m (and the syringe 970b) shown in FIG. 20A along line B-B;

FIG. 20C is a second cross-sectional view through the apparatus 600m (and the syringe 970a) shown in FIG. 20A along line C-C; and FIG. 20D is a third cross-sectional view through the apparatus 600m (and the syringes 970a and 970b) shown in FIG. 20A and FIG. 20B along line D-D.

DETAILED DESCRIPTION OF PREFERRED ASPECTS OF THE INVENTION

Figure 17C:
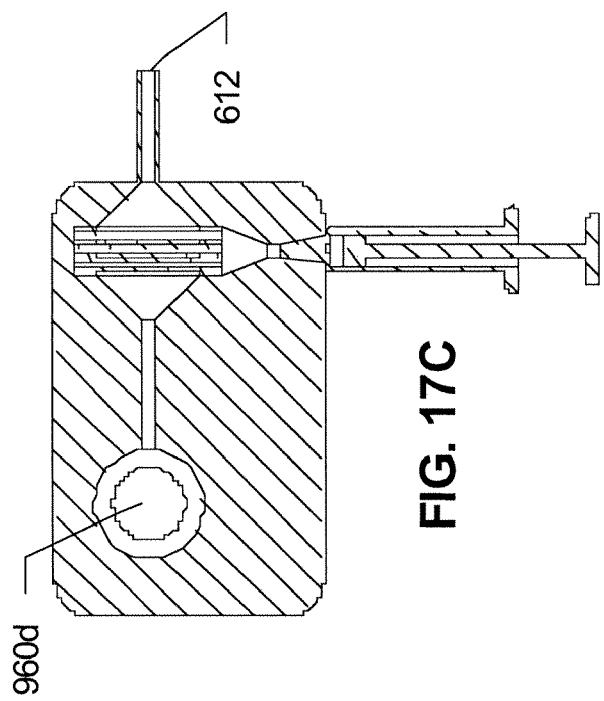
FIG. 17C is a second cross-sectional view through the apparatus 600n (and the syringe 970a) shown in FIG. 17A and FIG. 17B along line C-C.

Some embodiments of the invention provide one apparatus that is suitable for extraction of plasma from a whole blood sample, and also suitable for analysis of the plasma in the apparatus, using an analyzer or a meter, for example without any limitation, the meter 900 shown collectively in FIGS. 12A-12D. Some embodiments of the apparatus are used for collection of a blood sample directly from a body part, for example without any limitation, the apparatus 600e shown collectively in FIGS. 7A-7C. In apparatus 600e, the sharp open end 147 may be inserted directly into a blood vessel, and the pressure of the patient's blood provides the blood flow means.

The first eight embodiments of the invention provide an apparatus suitable for extraction of plasma from blood, and measurement of at least one analyte in the plasma. The ninth, tenth and eleventh embodiments of the invention provide an apparatus suitable for extracting plasma from whole blood, and the plasma is then tested by any analyzer.

Some embodiments of the apparatus comprise at least one whole blood flow path and one plasma flow path, for example apparatus 600a shown collectively in FIGS. 1A-1D. Those skilled in the art will appreciate that the apparatus could comprise more than two flow paths, for example, apparatus 600f shown collectively in FIGS. 11A-11C comprises two whole blood flow paths and one plasma flow path. A flow path is defined by a start end and a terminating end, and includes at least one chamber in fluid connectivity with the start end and a terminating end. Any other chambers in the flow path must be in series and in fluid connectivity with each other. Flow paths are identified in the examples shown. Some embodiments of the apparatus comprise a blood flow path and a plasma collection chamber, without any plasma or whole blood measurement means, for example without any limitation, the embodiments of the apparatus 600*m*, 600*n* and 600*p* illustrated collectively in FIGS. 16A-16D to FIGS. 20A-20D.

Since one function of the apparatus is to extract or filter plasma out of whole blood received from a blood supply, the blood flow path represents a blood compartment, and the plasma flow path or the plasma collection chamber represent a plasma compartment. The plasma compartment and the blood compartment are separated by a porous membrane. The side of the porous membrane in contact with the blood is referred to as the blood side, and the side of the porous membrane in contact with the plasma is referred to as the plasma side. Those skilled in the art will appreciate that when the blood side of the porous membrane is in contact with blood, the blood side is also in contact with the plasma in the whole blood because plasma is a natural component of whole blood. It should be understood that unless specified that the plasma is the plasma in the whole blood, the term plasma refers to the whole blood without the formed elements of the whole blood, i.e., the plasma extracted from the whole blood.

Plasma extraction is defined as the process of transferring plasma from whole blood in the filtration chamber (shown schematically as 634 in FIG. 18C, as an example) across the porous membrane, to the plasma collection chamber (shown schematically as 636 in FIG. 18C, as an example). As will be seen from the specific embodiments, the blood is drawn into a filtration chamber 634 by various means, and the plasma is extracted into a plasma collection chamber 636 by various means. The filtration chamber includes the blood side of the porous membrane, and the plasma collection chamber includes the plasma side of the porous membrane. The porous membrane of the embodiment of the invention illustrated collectively in FIGS. 18A-18D, is shown as 694 in FIG. 2F, and is an example where a hollow fiber filter bundle (shown as 660C in FIG. 18A). In this embodiment, the porous membrane 694 forms the wall of the hollow fiber filter. The compartmentalization of blood and plasma is more easily illustrated collectively in FIGS. 3A-3F. In this particular embodiment, the porous membrane 694 is flat, and the plasma collection chamber 636 is shown as 636*a*. In this particular embodiment, the chamber 636*b*, may be considered to be an extension of the chamber 636*a*. The porous membrane 694 is arranged within the housing of the apparatus to form a barrier between the whole blood and the plasma extracted from the whole blood.

Those skilled in the art will appreciate that hematocrit of the whole blood in the blood flow path, downstream of the filtration chamber, will be altered after plasma filters through the porous membrane into the plasma collection chamber, and It should be understood that the blood with the altered hematocrit is still referred to as whole blood or blood. However, for clarity the term filtered blood is sometimes used to refer to the blood in the blood flow path that flows out of the filtration chamber, i.e., the blood downstream of the filtration chamber.

A second function of some embodiments of the apparatus is to generate and provide signals to the meter processor for measurement of at least one analyte in the extracted plasma. In the examples described, the signal providing means include at least an optical chamber having at least one optical window for performing spectroscopic measurement (or spectroscopy), or a biosensor chamber comprising at least one biosensor in contact with the plasma.

Depending on the design of the apparatus, as will be seen from the examples described later in details, the blood sample can enter the body 123 of the apparatus by any of the following means, or combination thereof: a) negative pressure generating means within the blood flow path, for example, negative pressure can be generated by squeezing and releasing flexible members included in a compressible chamber located at the end of the flow path, and negative pressure can also be generated by pulling on the previously pushed in plunger of a syringe attached to an open end in the body of the apparatus, located at the end of the flow path; b) capillary action within the flow paths; c) positive pressure generating means within the blood flow path, for example, positive pressure can be generated by pushing against the previously pulled out plunger of a syringe attached to an open end in the body of the apparatus, located at the beginning of the flow path, wherein the syringe contains the blood sample previously aspirated therein, or positive pressure can also be derived from the pressure of blood within a vessel, for example without any limitations, veins, arteries, any compressible vessel or a vessel with a compressible part, an arterial line, and a venous line. Positive pressure derived from a blood vessel is particularly useful when the inlet open end of the apparatus is a sharp open end 147 of a needle, illustrated collectively in FIGS. 7A-7C as a non-limiting example. The positive pressure from a syringe is usually applied at the inlet open end of the apparatus, for example, inlet open end 612 of apparatus 600*d*, illustrated collectively in FIGS. 6A-6E. However, the syringe 970*b* illustrated collectively in FIGS. 20A, 20*b* and 20D, can be used to apply either positive or negative pressure, in order to create the blood flow means.

An essential feature of the apparatus is a flow-through filtration chamber comprising a porous membrane, sometimes simply referred to as a membrane. The membrane has optional shapes and sizes, and includes a wall with a wall thickness, and pores through the wall of the membrane. In the description of the specific embodiments, the filtration chamber 634 refers to the section of the blood flow path that includes the blood side of the membrane. Moreover, the membrane can be assembled in different ways, as illustrated in the non-limiting examples of various embodiments of the invention. Plasma extraction, previously defined as the process of transferring plasma from whole blood in the filtration chamber across the porous membrane to the plasma collection chamber, is enhanced by the following: a) increased blood flow along the blood side of the membrane; b) increased size and number of pores in the membrane; c) decreased membrane wall thickness; d) increased surface area of the membrane; and e) applying negative pressure to the plasma side of the membrane. Those skilled in the art will appreciate that these features should be optimized for efficient plasma extraction, depending on the analyte measurement required. For example, increased blood flow decreases the apparent viscosity of the blood, but if the flow is too forceful, hemolysis could occur. Also, if the pores are too large, the formed elements of blood (e.g., red blood cells) could filter through with the plasma. Furthermore, the formed elements of blood could plug up the pores, hindering plasma filtration, and hemolysis could occur as the red blood cells squeeze through the pores. Plasma extraction means, as described in some embodiments of the invention, refer to the means of generating the negative pressure to the plasma side of the porous membrane.

The measurement techniques shown as non-limiting examples include spectroscopic measurement and biosensor measurement. The terms testing a sample, sample analysis, and analyzing a sample, are sometimes used instead of the term measuring a sample, and those skilled in the art will appreciate that these terms mean, providing information about a sample, for example, the bilirubin (a non-limiting example of an analyte) concentration in the sample, or the hemoglobin oxygen saturation (a non-limiting example of the ratio of different analyte concentrations).

Some embodiments of the invention provide measurements of plasma, as well as the whole blood used to provide the plasma, and some embodiments do not provide any measurement of either plasma or the whole blood.

Some embodiments of the meter may include some of the following:

a) a meter housing;
b) a power supply, which is preferably in the form of rechargeable batteries;
c) a source of electromagnetic radiation (EMR);
d) a slot in the meter housing for receiving the apparatus, the slot having an electrical input contact for mating with the electrical output contact of the apparatus when the apparatus is inserted into the slot. When the electrical input contact mates with the electrical output contact of the apparatus, the optical chamber becomes positioned to receive the EMR from the source. Also, sample biosensor data is generated after the electrical input contact mates with the electrical output contact of the apparatus, and the sample is in contact with the biosensor;
e) a photodetector for measuring EMR transmitted through or reflected from the sample within the optical chamber and for providing an EMR-based signal derived from the EMR transmitted through or reflected from the sample; and
f) a processor in communication with the photodetector for receiving the EMR-based signal, and the input contact for receiving the sample biosensor data. The EMR-based signal is used to prepare a spectroscopic test result, and the sample biosensor data is used to prepare a biosensor test result. A test result is also referred to as an analyte measurement.

Some embodiments of the meter comprise one photodetector or photodiode, or more than one photodetector (shown as an inclusion in part 890) assembled as an array of detectors in a spectrometer. A spectrometer using an array of detectors also comprises a grating for dispersing EMR emerging from the sample, into wavelength components. The meter optionally comprises a focusing lens between the apparatus and the photodetector, show as 870 in FIGS. 12A & 12C and FIGS. 13A & 13C. Some embodiments of the meter only perform spectroscopic measurements, and the signal providing means in the apparatus comprises an optical chamber within the housing of the apparatus, for receiving the extracted plasma, the optical chamber having at least one optical window for spectroscopic measurement. Alternatively, some embodiments of the meter only perform biosensor measurements, and the signal providing means in the apparatus comprises a biosensor chamber within the housing of the apparatus, for receiving the extracted plasma, the biosensor chamber having at least one biosensor for biosensor measurement.

The biosensor chamber is located along a flow path, and the biosensor chamber may have one or more than one biosensor for analyzing the plasma sample. Optionally, the apparatus contains more than one biosensor chamber as illustrated in FIG. 6E, identified as 672 (a plasma biosensor chamber) and 674 (a whole blood biosensor chamber). A flow path that includes a biosensor chamber is specifically designed with at least one active surface of the biosensor exposed to the sample. Those skilled in the art will appreciate that biosensors may include various transducer arrangements that convert at least one property of the sample into an electrical signal, wherein the transducer comprises at least one active surface for contacting the sample. As non-limiting examples, the at least one active surface is one of a chemical sensitive surface, or an ionic sensitive surface, and wherein the at least one biosensor comprises at least one of a transistor, an ion-selective membrane, a membrane-bound enzyme, a membrane-bound antigen, a membrane-bound antibody, or a membrane-bound strand of nucleic acid. The apparatus also comprises at least one electrical output contact, for example 654c illustrated in FIG. 1D, which is electrically connected to the biosensor 652c by an electrical conductor 676C. The apparatus slot of the meter, for example 800 illustrated collectively in FIG. 12A to FIG. 13C comprises two electrical input contacts 854a and 854b. When the electrical output contacts from a suitable apparatus mate with a corresponding electrical input contact after the apparatus is properly inserted into the slot, the optical chamber is positioned to receive EMR from its source. Although the example shows the apparatus electrical output contact in a female configuration, and also shows the meter slot electrical input contact in a male configuration, those skilled in the art will appreciate that the electrical output contacts can mate with the electrical input contacts in other ways.

In some embodiments of apparatus, the biosensors require calibration prior to sample measurement, and in some embodiments, the biosensors are pre-calibrated. Pre-calibration is usually performed for a lot or batch of apparatus, and a barcode on the apparatus could contain calibration information, which is read by a barcode reader that is linked to the processor of the meter. In the embodiments of the apparatus that require calibration prior to sample measurement, calibration of biosensors is performed by flooding the biosensor chamber with an appropriate calibration fluid stored in a sealed calibration reservoir or pouch in a cavity of the apparatus (not shown). In an embodiment of the meter where calibration of the biosensor is required for the individual apparatus, prior to sample measurement, the meter also comprises a means for rupturing the calibration pouch and delivering the calibration fluid to the biosensor(s) in the biosensor chamber. Those skilled in the art will appreciate that the electrical signals generated from the biosensor after it comes in contact with a calibration fluid of know composition, and the known concentration of the analyte in the calibration fluid, can be used to generate a calibration algorithm for the analyte, and therefore for the sake of brevity, the mathematics involved in biosensor calibration will not be discussed here. The biosensor calibration requires mating of the electrical output contact of the apparatus and the electrical input contact of the meter slot.

Moreover, where calibration of the biosensor is required, capillary breaks are provided along the flow path at strategic locations, for retaining the calibration fluid in the biosensor chamber (not shown). Sometimes a capillary break, located along the flow path between the inlet open end and the biosensor chamber (not shown), is used to retain the fluid sample away from the biosensor, prior to sample measurement. A capillary break is defined as an expansion in the flow path, which makes the flow path too large at the point of expansion to maintain fluid flow by capillary action. In some embodiments, where flow does not depend on capillary action, references are still made to capillary breaks. In such cases, the structure referred to as a capillary break, is simply an expansion in the flow path that functions as a buffer chamber for collecting excess fluid. After biosensor calibration, the fluid sample is used to flush out the calibration fluid from the biosensor chamber, and bring the fluid sample in contact with the biosensor. Those skilled in the art will appreciate the methods used to flush out the calibration fluid with sample, and for the sake of brevity, the methods will not be discussed here.

Some embodiments of apparatus are shown with vents for relieving pressure inside the flow paths, or facilitating airflow out of the flow paths. Other embodiments of the apparatus are shown, where there are no vents for facilitating airflow out of the flow path. Instead of the vent, the housing of the apparatus includes a compressible chamber located at the end of the flow path, replacing the vent(s), and means for generating negative pressure within the chamber. In some embodiments, two separate compressible chambers (for example 960a and 960b shown in FIG. 4D) are located close to each other, without being fluidly connected, so that one set of flexible members (for example 962a and 962b shown in FIG. 4B) can be used to generate negative pressure simultaneously in the two separate compressible chambers. In some embodiments, two or more compressible chambers are fluidly connected or merged into one compressible chamber. It should be understood that having two compressible chambers fluidly connected, is equivalent to merging the two compressible chambers into one compressible chamber. Those skilled in the art will appreciate that other embodiments of apparatus can operate with a combination of at least one vent and at least one compressible chamber. Also, a single flexible member, for example, either 962a or 962b, can be used instead of both 962a and 962b, in order to generate a negative pressure.

In some embodiments, the interior walls of the apparatus are treated with a hydrophilic coating to promote even spreading of the blood within the optical chamber, and to promote movement of blood along the flow path. A flow path may also contain one or more reagents, anywhere along the flow path, for example without limitation, an anticoagulant, a hemolyzing reagent, or a reagent that reacts with an analyte to enhance the absorbance of EMR. In some use of the apparatus, anticoagulated blood is collected in a microtube, for example, blood collected from the heel of a neonate after a pin or lancet prick, for diagnosing and treating neonatal jaundice. Ordinarily the blood is sent to the central lab for centrifugation, and bilirubin is measured in the plasma using a lab blood analyzer. In this example, there is no need for an anticoagulant anywhere inside the apparatus, because the blood is already collected in a microtube containing an anticoagulant.

In using the anticoagulated blood from the neonate, a preferred embodiment of the apparatus is one like apparatus 600h, illustrated collectively in FIGS. 15A-15E. Before drawing the blood into the apparatus 600h, the flexible members 962a and 962b are squeezed between the fingers of the user in order to dispel air from the compressible chambers 960a and 960b. Subsequently, the inlet open end 612 is inserted in the blood supply, i.e., the blood sample in the microtube. Those skilled in the art will appreciate that the length of the piece of capillary tubing 672b must be optimized so that the inlet open end can at least reach close to the bottom of the microtube, and to provide a blood barrier between the filtration chamber 634 and the atmosphere. The blood barrier will prevent air from being sucked into the plasma measurement chamber, for example, the optical chamber 616b shown in FIG. 15C.

Once the inlet open end 612 is submerged in the blood contained in the microtube, pressure on the compressible chambers 960a and 960b is released slowly, allowing blood to be drawn into the blood flow path, and plasma to be extracted into the plasma flow path. Those skilled in the art will appreciate that the draw from the compressible chambers 960a and 960b, and the rebound of the flexible members 962a and 962b could be optimized, so that the pressure on the flexible members 962a and 962b does not have to be released slowly. In a particular embodiment, the draw from compressible chamber 960a is greater than the draw from the compressible chamber 960b.

Preferably, the plasma flow path, and in particular the inside walls of the optical chamber 616b, is coated with a hydrophilic material, in order to promote even spreading of the plasma in the optical chamber 616b. Those skilled in the art will appreciate that calibration algorithm for the spectroscopic measurement of bilirubin, as a non-limiting example, can be developed using calibration samples containing air bubbles in the optical chamber 616b, enabling the meter to measure bilirubin in samples with inclusion of air bubbles in the optical chamber, with minimal errors. Therefore, exclusion of air bubbles for bilirubin measurement is not essential.

When an apparatus comprising both facilities for spectroscopic measurement and facitilies for biosensor measurement is inserted properly in the slot of the meter, the electrical output contact of the apparatus mates with the electrical input contact of the meter slot, bringing the optical chamber of the apparatus in position to receive EMR from the EMR source. Those skilled in the art will appreciate that the EMR could also be channeled to the optical chamber by optical fibers. The EMR transmitted through the fluid sample in the apparatus, or reflected from the fluid sample, impinges upon a photodetector within the meter. Calibration algorithms for biosensor measurements are preferably installed within the processor of the meter, for transforming the biosensor signals into analyte measurements, but some biosensors require calibration prior to sample measurement, as mentioned before.

Those skilled in the art will appreciate the various ways a spectroscopic measurement instrument can be constructed, and various elements that make up such instruments. Accordingly, for the sake of brevity, description of basic spectroscopy and a list and function of the elements that make up a spectroscopic device will not be discussed here. However, it should be noted that a joint-diagnostic spectroscopic and biosensor meter, requires at least one source of EMR, and the preferred source of EMR is a tungsten lamp, but without limitation, the source of EMR may include one or more than one Light Emitting Diode (LED), one or more than one laser, or combination thereof. Those skilled in the art will appreciate that when the source of EMR is a single source, the single source could be split by a multi-channel optical fiber for providing more than one light path.

With respect to the detection system, the preferred detector is an array of photodiodes, but those skilled in the art will appreciate that other detection systems may be used, for example without any limitations, a single photodiode or one or more than one charged coupled detector (CCD) may be used.

With respect to spectroscopic measurements, the examples shown describe a meter that operates in transmission mode. Those skilled in the art will appreciate that the meter can also operate in reflectance mode by placing a reflecting member in the apparatus slot, adjacent to one side of the optical chamber 616b (FIG. 15A and FIG. 15C), such that the EMR transmitted through the sample would be reflected off the reflecting member, and the reflected EMR would enter the sample for the second time. In a meter operating in the reflectance mode, both the EMR source and the photodetector would be on the same side of the optical chamber 616b. Moreover, those skilled in the art will also appreciate that instead of installing a reflecting member around the slot in the housing of the meter, one side of the wall-portions 626a or 626b of the optical chamber 616b, for example as shown in FIGS. 15A-15E, could be coated with a reflecting material. Preferably the depth of the optical chamber, i.e., the internal distance between the optical windows, is about 0.1 mm for a blood sample, but the depth of the optical chamber is preferably larger for plasma, due to the absence light-scattering caused by the red blood cells. An average depth of an optical chamber is in an approximate range of about 0.02 mm to about 5 mm.

In some embodiments, the meter further comprises a display screen for viewing the results and aiding the operator using the meter, as well as buttons for manipulating the display function. Those skilled in the art will appreciate that the meter could be connected to a host computer. Therefore, some embodiments of the system also comprise at least one communication port for interfacing with other instruments, or a wireless communication system. Other non-limiting examples of other instruments include a printer, and diagnostic testing instruments like a pulse oximeter or some other non-invasive testing instrument. The optional communication port is also used to upgrade information in the meter's processor, as well as to download information from the meter's processor. Another optional port in the housing of some embodiments of the joint-diagnostic spectroscopic and biosensor meter is provided for charging the power supply within the meter. Those skilled in the art will appreciate that a single port can be used for both data transfer and a power supply, for example without any limitation, a USB (Universal Serial Bus) port.

In a preferred embodiment of an apparatus 600a illustrated collectively in FIGS. 1A-1D, the apparatus includes a flow-through filtration chamber 634, which comprises a hollow fiber filter bundle 660a. Details of the hollow fiber filter bundle 660a are illustrated collectively in FIGS. 2A-2G. The hollow fiber filters in the hollow fiber filter bundle 660a run orthogonal (or approximately orthogonal in some embodiments) to the blood flow in the blood flow path. In an alternative apparatus 600c illustrated collectively in FIGS. 4C-4D, the hollow fiber filters in the hollow fiber filter bundle 660b runs in parallel (or approximately parallel in some embodiments) with the blood flow in the blood flow path. Details of the hollow fiber filter bundle 660b are illustrated collectively in FIGS. 5A-5E.

In some embodiments, the inlet chamber 670 of the apparatus, illustrated collectively in FIGS. 6A-6E is configured to accommodate the male end of a syringe. In other embodiments, the inlet portion of the apparatus is also configured to resemble a piece of capillary tube, for example 672 illustrated collectively in FIGS. 1A-1D, to receive the blood sample from a pin prick drop of blood, through the inlet open end 612. As an alternative, the inlet open end of the apparatus is the sharp end 147 of a hollow needle, as illustrated collectively in FIGS. 7A-7C. The hollow needle is allowed to enter the lumen of a vessel, for example a blood vessel, for receiving the blood directly into the apparatus, eliminating the need of a syringe. The shaft 143 of the hollow needle 100, illustrated collectively in FIGS. 8A-8F is preferably encased in a moveable barrel 200, illustrated collectively in FIGS. 9A-9F, for sheathing and unsheathing the shaft 143 of the hollow needle 100, to protect the user from accidental injury. A non-limiting example of a hollow needle 100, a barrel 200, and a hollow needle assembly 300, are illustrated collectively in FIGS. 8A-8F, FIGS. 9A-9F and FIGS. 10A-10F respectively. Other embodiments of similar needles are disclosed in U.S. patent application Ser. No. 11/738,889 (Samsoondar, the entire contents of which are incorporated herein by reference). The outlet 171 of the hollow needle assembly 300, illustrated collectively in FIGS. 10A-10F, mates with the inlet chamber 670 of the apparatus illustrated collectively in FIGS. 6A-6E, eliminating the need of a syringe. The apparatus could be inserted into the meter slot, with the hollow needle assembly 300 still attached. As another alternative, as illustrated collectively in FIGS. 14A-14E, the inlet chamber 670 is flared so that the inlet open end 612 can be placed over a pin prick, either before but preferably after the drop of blood develops. The blood is then allowed to freely flow into the apparatus. The flow may be assisted by some squeezing of the body part around the pin prick. It is well known that excessive squeezing, commonly referred to as milking, should be avoided if contamination of the blood with interstitial fluid compromises the accuracy of the analyte being measured.

In an embodiment illustrated in FIG. 11A, comprising several measurement chambers, the distance (shown as A) from the blood optical chamber to its adjacent edge of the apparatus, is approximately equal to the distance (shown as B) from the plasma optical chamber to its adjacent edge of the apparatus. An embodiment of a meter designed to operate with such an apparatus, optionally comprises one source of EMR and one light path. The EMR in the single light path travels through the first optical chamber when the apparatus is inserted properly in a first orientation. When the apparatus is inserted properly in a second orientation, the second orientation being 180 degrees to the first orientation, the single light path travels through the second optical chamber. Therefore, the plasma and the whole blood can be measured sequentially using the same light path. Because of the absorbance signals for whole blood and plasma are significantly different, the software in the meter discriminates whole blood from plasma. Those skilled in the art will appreciate that there are other methods of analyzing the plasma and whole blood using a single light path, for example, a prompt in the display screen could provide appropriate instructions for insertion of the apparatus.

Other embodiments are described, illustrated collectively in FIGS. 16A-16D, 17A-17D, 18A-18D, 19A-19D, and 20A-20D that cannot be used to analyze the blood or the extracted plasma, and the plasma has to be removed from the apparatus for analyte measurement by an analyzer.

Referring collectively to FIGS. 1A-1D, shown are schematic drawings illustrating details of an apparatus 600a that is suitable for both extraction of plasma from a whole blood sample, and plasma measurement according to a first embodiment of the invention.

FIG. 1A shows a top view of the apparatus 600a, FIG. 1B shows a first cross-sectional view through the apparatus 600a shown in FIG. 1A along line B-B, FIG. 1C shows a second cross-sectional view through the apparatus 600a shown in FIG. 1A along line C-C, and FIG. 1D shows a third cross-sectional view through the apparatus 600a shown in FIG. 1A and FIG. 1B along line D-D. The apparatus 600a includes a housing 123, defining: a whole blood flow path beginning at the inlet open end 612 (the start end), and terminating at the compressible chamber 960a (the terminating end); and a plasma flow path beginning at the plasma collection chamber 636 (the start end) and terminating at the compressible chamber 960b (the terminating end). As shown in the whole blood flow path, are the inlet open end 612, the inlet chamber 670 for receiving blood through the inlet open end 612, the filtration chamber 634, the filtration chamber outflow 620a, and the compressible chamber 960a, fluidly connected in series. The filtration chamber 634 includes the blood side of the porous membrane of the hollow fiber bundle 660a, which is shown in details in FIGS. 2A-2G. As shown in the plasma flow path, are the plasma collection chamber 636, the plasma biosensor chamber 672 (the plasma measurement chamber), the plasma biosensor chamber outflow 620c, and the compressible chamber 960b, fluidly connected in series. The plasma collection chamber 636 includes the plasma side of the porous membrane of the hollow fiber bundle 660a. Regarding the whole blood flow path, those skilled in the art will appreciate that the inlet chamber 670, the filtration chamber 634, and the outflow 620a may be considered collectively as the filtration chamber. Regarding the plasma flow path, those skilled in the art will appreciate that the plasma collection chamber 636, the plasma biosensor chamber 672, and the plasma outflow 620c may be considered collectively as the plasma collection chamber. Moreover, those skilled in the art will also appreciate that although some parts shown are not essential, or two or more parts overlap, the various parts or labels are sometimes included for clarity. In the embodiment of the apparatus 600a, the measurement technique uses a single biosensor, but other embodiments include more than one biosensor, and some embodiments include an optical chamber for spectroscopic measurement, instead of a biosensor chamber. As an example, an optical chamber 616b is shown in the embodiment 600b, illustrated collectively in FIGS. 3A-3F.

With further reference to FIGS. 1A-1D, shown is the plasma collection chamber outflow 620a, terminating at the compressible chamber 960a. The compressible chamber 960a is a cavity in the housing 123 with flexible members 962a and 962b. By manually squeezing and releasing the flexible members 962a and 962b, negative pressure is generated in the compressible chambers 960a and 960b. The only open end in apparatus 600a is the inlet open end 612, and those skilled in the art will appreciate that the inlet open end 612 can be capped to avoid contaminating the apparatus with blood. As a non limiting example, a cap 960 is illustrated collectively in FIGS. 15A-15E. Those skilled in the art will appreciate that one flexible member (962a or 962b) could perform the same function. In this embodiment, by squeezing the flexible members 962a and 962b, negative pressure is also generated in both compressible chambers 960a and 960b, for ease of use. The volume of the compressible chambers 960a and 960b, and the maximum depression of the flexible members 962a and 962b, determines the maximum volume of fluids that could be drawn into the flow paths. Also, the rigidity of the flexible members 962a and 962b, which contributes to the rate at which the members 962a and 962b are restored to their original shape after squeezing and releasing, i.e. the rebound of the flexible members 962a and 962b, determines the velocity of the fluids in the flow paths. In some embodiments, for example apparatus 600f illustrated collectively in FIGS. 11A-11C, the three flow paths converge into a single compressible chamber 960d. Those skilled in the art will appreciate that in another embodiment, compressible chambers 960a and 960b could be merged into a single compressible chamber.

To test a patient's blood, the flexible members 962a and 962b must first be squeezed, preferably between the thumb and the index finger, to dispel air from the compressible chambers 960a and 960b. With air inside the compressible chambers 960a and 960b dispelled, the inlet open end 612 of the apparatus 600a is then inserted into a blood supply, which could be a drop of blood on the patient's skin generated from a pin prick, or anticoagulated blood in a microtube (a small tube, usually used for neonatal blood collection). To draw the blood into the apparatus 600a, the flexible members 962a and 962b must be released, creating negative pressure within the compressible chambers 960a and 960b. Preferably, the flexible members 962a and 962b are released slowly, to maintain the inlet chamber 670 filled with blood. The negative pressure within the compressible chamber 960a causes blood to flow in the blood flow path towards the compressible chamber 960a; the blood flow decreases the apparent viscosity of the blood and reduces compaction of the red blood cells in the hollow fiber filter 660a. The extraction of plasma from the blood is enhanced by: capillary action within the various chambers defined in the housing 123, the negative pressure created in the compressible chamber 960b, the negative pressure created in the compressible chamber 960a, the surface area of the porous membranes 694 (FIG. 2F) of the hollow fiber filters 660a (also shown as 694 in FIG. 3F, where the membrane is flat), the pore size in the membrane 694, and the wall thickness of the porous membrane 694. The surface area of the porous membrane 694 is increased by increasing the number of hollow fiber filters. In the preferred embodiment, the membrane is configured in a bundle of hollow fiber filters.

Referring collectively to FIGS. 2A-2G, shown are schematic drawings illustrating details of the hollow fiber filter 660a (also referred to as a hollow fiber filter bundle) shown inside the body 123 of the apparatus 600a illustrated collectively in FIGS. 1A-1D. The hollow fiber filter bundle 660a in this embodiment comprises seven hollow fiber filters, held together by two flanges 682 and 684.

Referring to FIG. 2A, shown is a top view of the hollow fiber filter bundle 660a, illustrating the perforated flange 684, and the closed flanged 682, and identifying a single hollow fiber filter 696.

Referring to FIG. 2B, shown is a left side view of the hollow fiber filter bundle 660a, illustrating the perforated flange 684, and identifying the lumen 692 of a single hollow fiber filter.

Referring to FIG. 2C, shown is a right side view of the hollow fiber filter bundle 660a, illustrating the closed flange 682. The periphery of the flanges 682 and 684 are sealed in the body 123 of the apparatus 600a, to prevent whole blood from moving from the filtration chamber 634 into the plasma collection chamber 636 (FIG. 1D). In this embodiment of the apparatus, the flanges are a schematic representation of the seal between the blood compartment or the blood flow path, and the plasma compartment or the plasma flow path. From a manufacturing perspective, it is preferred that the hollow fiber filters are assembled in bundles (e.g. 660a), and sandwiched in position between the top and bottom halves of the apparatus.

Referring to FIG. 2D, shown is a cross-sectional view through the hollow fiber filter bundle 660a shown in FIG. 2A along line D-D, showing the closed flange 682, the cross-section of the hollow fiber filters, and detail F.

Referring to FIG. 2E, shown is a perspective view of the hollow fiber filter bundle 660a, showing a clear view of the perforated flange 684.

Referring to FIG. 2F, shown is a detailed view of the cross-section of a single hollow fiber, according to detail F identified in FIG. 2D, showing the lumen 692 of the hollow fiber filter, and the wall 694 of the hollow fiber filter.

Referring to FIG. 2G, shown is an alternative perspective view of the hollow fiber filter bundle 660a, showing a clear view of the closed flange 682. As an example, seven hollow fiber filters are shown tightly inserted inside perforations in the flange 684, and sealed at the juncture of the hollow fibers and the flange 682. The wall 694 of the fiber is porous, and in some embodiments, the pores have an approximate distribution of pore diameters ranging from about 0.1 micrometer to about 30 micrometers, and in some embodiments the thickness of the wall 694 ranges from about 0.1 mm to about 0.5 mm. In some embodiments, the internal diameter of the hollow fiber filters ranges approximately from about 0.1 mm to about 1 mm. Those skilled in the art will appreciate that various combination of pore sizes, wall thicknesses, and internal diameters of the hollow fiber filters could be used, and are within the scope of the invention.

Those skilled in the art will appreciate the membrane 694 in the first embodiment of the invention is a partition between the blood compartment, and the plasma compartment. In this embodiment, the blood compartment and the blood flow path are the same, and include the filtration chamber 634, and the plasma compartment and the plasma flow path are the same, and include the plasma collection chamber 636. Moreover, the plasma compartment includes the lumen 692 of the hollow fiber filters, and the blood compartment includes the exterior of the hollow fiber filters. A reversed design is illustrated collectively in FIGS. 4A-4D, where the blood compartment includes the lumen of the hollow fiber filters, both flanges identified as 684a and 684b (illustrated collectively in FIGS. 5A-5E) are perforated, and the plasma compartment includes the exterior surface of the hollow fiber filters. The blood and plasma compartments are seen more clearly in a second embodiment of the apparatus 600b, illustrated collectively in FIGS. 3A-3F. In apparatus 600b, the membrane 694 is not arranged as hollow fiber filters, but instead is a flat member erected as a partition between the blood compartment (illustrated as the chamber 634) and the plasma compartment (illustrated as the chamber 636a). These embodiments will be described in more details later.

In a preferred embodiment, at least the first section of the whole blood flow path is coated with an appropriate anticoagulant, to minimize clotting and promote fluidity of the blood. Fluidity of the blood provides more efficient plasma extraction. However, when the blood sample is anticoagulated blood (i.e., blood mixed with an anticoagulant, for example, heparin) in a tube, an anticoagulant within the flow paths of the apparatus is not essential.

Referring collectively to FIGS. 3A-3F, shown are schematic drawings illustrating details of a whole blood and plasma apparatus 600b that is suitable for both extraction of plasma from a whole blood sample, and plasma analyte measurement according to a second embodiment of the invention.

FIG. 3A shows a top view of the apparatus 600b, FIG. 3B shows a first cross-sectional view through the apparatus 600b shown in FIG. 3A along line B-B, FIG. 3C shows a second cross-sectional view through the apparatus 600b shown in FIG. 3A along line C-C, FIG. 3D shows a third cross-sectional view through the apparatus 600b shown in FIG. 3A along line D-D, FIG. 3E shows a fourth cross-sectional view through the apparatus 600b shown in FIG. 3A and FIG. 3B along line E-E, and FIG. 3F shows a detailed view of the detail F shown in FIG. 3C. The apparatus 600b illustrated collectively in FIGS. 3A-3F is similar to the apparatus illustrated collectively in FIGS. 1A-1D, and accordingly, elements common to them share common reference numerals. The first difference is that apparatus 600b has a combination of a vent 137a at the terminating end of the whole blood flow path, and a compressible chamber 960c at the terminating end of the plasma flow path. The second difference is that the filtration chamber comprises a flat membrane 694 instead of the hollow fiber filter bundle 660a shown in FIGS. 1C and 1D. The filtration chamber 634 is seen clearly as a section of the whole blood flow path in contact with the membrane 694, and is a section of the blood compartment. The plasma collection chamber is represented collectively by chambers 636a and 636b; the chamber identified as 636a represents the section of the plasma compartment that is in contact with the membrane 694. Those skilled in the art will appreciate that chamber 636b could be considered as an extension of chamber 636a. The third difference is that instead of a biosensor, the measurement facility includes an optical chamber 616b for spectroscopic measurement, with optical wall-portions 626a and 626b.

In the embodiment illustrated collectively in FIGS. 3A-3F, capillary action causes the blood to flow along the whole blood flow path, and the negative pressure generated by compressing and releasing the flexible members 962a and 962b, facilitates plasma extraction and causes the plasma to flow towards the compressible chamber 960c. It should be understood that the examples shown do not represent all the possible combinations of vents and compressible chambers, and therefore, the examples should not limit the scope of the present invention.

Referring collectively to FIGS. 4A-4D, shown are schematic drawings illustrating details of an apparatus 600c that is suitable for both extraction of plasma from a whole blood sample, and plasma measurement according to a third embodiment of the invention.

FIG. 4A shows a top view of the apparatus 600c, FIG. 4B shows a first cross-sectional view through the apparatus 600c shown in FIG. 4A along line B-B, FIG. 4C shows a second cross-sectional view through the apparatus 600c shown in FIG. 4A along line C-C, and FIG. 4D shows a third cross-sectional view through the apparatus 600c shown in FIG. 4A and FIG. 4B along line D-D. The apparatus 600c illustrated collectively in FIGS. 4A-4D is similar to apparatus 600a illustrated collectively in FIGS. 1A-1D, and accordingly, elements common to them share common reference numerals. The major difference is that both flanges 684a and 684b in the fiber bundle 660b are perforated (illustrated collectively in FIGS. 5A-5E in details), and the whole blood flows through the hollow fiber filters instead of around the hollow fiber filters. A second difference is the plasma measurement facility comprises an optical chamber 616b shown in FIG. 4D. Those skilled in the art will appreciate that the lumen 692 shown in FIG. 5D of the hollow fiber filters should be larger than the lumen 692 shown in the embodiment illustrated in FIGS. 2A-2G, to avoid compaction of red blood cells in the lumen of the hollow fiber filters.

Referring collectively to FIGS. 5A-5E, shown are schematic drawings illustrating details of an embodiment of a hollow fiber filter bundle 660b shown in apparatus 600c illustrated collectively in FIGS. 4A-4D.

FIG. 5A shows a top view of the hollow fiber filter bundle 660b, FIG. 5B shows a perspective view of the hollow fiber filter bundle 660b, showing a first perforated flange 684a in clear view, FIG. 5C shows an alternative perspective view of the hollow fiber filter bundle 660b, showing a second perforated flange 684b in clear view, FIG. 5D shows a cross-sectional view through the hollow fiber filter bundle 660b shown in FIG. 5A along line D-D, and FIG. 5E shows a detailed view of the detail E shown in FIG. 5D. The hollow fiber filter bundle 660b illustrated collectively in FIGS. 5A-5E is similar to the apparatus illustrated collectively in FIGS. 2A-2G, and accordingly, elements common to them share common reference numerals. The major differences are that both flanges 684a and 684b are perforated, and hollow fiber filter bundle 660b comprises four hollow fiber filters instead of seven. Because blood flows inside the hollow fibers in the embodiment 660b of a hollow fiber filter bundle, the internal diameter of the fibers in the embodiment 660b should be substantially larger than the internal diameter of the fibers in the embodiment 660a illustrated in FIGS. 2A-2G.

Referring collectively to FIGS. 6A-6E, shown are schematic drawings illustrating details of an apparatus 600d that is suitable for both extraction of plasma from a whole blood sample, and whole blood and plasma measurement according to a fourth embodiment of the invention.

FIG. 6A shows a top view of the housing 123 of the apparatus 600d showing the inlet open end 612, the inlet chamber 670, a whole blood optical chamber wall-portion 624a, and a plasma optical chamber wall-portion 626a. The apparatus 600d comprises three flow paths shown more clearly in FIG. 6E.

FIG. 6B shows a first cross-sectional view through apparatus 600d illustrated in FIG. 6A along line B-B, showing parts identified later in FIG. 6E.

FIG. 6C shows a second cross-sectional view through apparatus 600d illustrated in FIG. 6A along line C-C, showing parts identified later in FIG. 6E. In addition, shown are the conduits 135a, 135b and 135c which connect the capillary breaks 622a, 622b and 622c, with the respective vents 137a, 137b and 137c.

FIG. 6D shows a third cross-sectional view through apparatus 600d illustrated in FIG. 6A along line D-D, showing parts identified later in FIG. 6E. In addition, shown are the blood optical wall portions 624a and 624b. For convenience and as deemed appropriate, similar reference numerals are used as those used for the apparatus 600d illustrated previously, and similar reference numerals will also be used for other embodiments as deemed appropriate.

FIG. 6E shows a fourth cross-sectional view through apparatus 600d illustrated in FIG. 6A and FIG. 6D along line E-E. The apparatus 600d can be filled with blood from a traditional syringe, after the male end of the syringe is inserted through the inlet open end 612, into the inlet chamber 670. Alternatively, the male end 171 of the hollow needle 100 illustrated collectively in FIGS. 8A-8F is first fitted into the apparatus inlet chamber 670; the sharp open end 147 of the hollow needle is then inserted into a blood vessel, allowing the blood to flow into the apparatus 600d. The hollow needle 100 assembled with a safety barrel 200 (shown collectively in FIGS. 9A-9F) is also shown collectively in FIGS. 10A-10F as 300. Whether a traditional syringe or the needle 100 illustrated collectively in FIGS. 8A-8F and FIGS. 10A-10F is used, the blood arrives first at the manifold 640; from the manifold 640, the blood is distributed into two whole blood flow paths, which begin at the manifold 640: the first flow path includes in series, the whole blood biosensor inlet transition chamber 642, the whole blood biosensor chamber 674, the whole blood biosensor outflow chamber 620b, the whole blood biosensor capillary break 622b, and terminating at the whole blood biosensor vent 137b via a conduit 135b; the second flow path, which also begins at the manifold 640, includes in series, the whole blood spectroscopic inlet transition chamber 614a, the whole blood optical chamber 616a, the whole blood spectroscopic overflow chamber 618a, the filtration chamber 634 (for extracting plasma from the whole blood using the hollow fiber filter bundle 660a with closed flange 682 shown; details of 660a are shown collectively in FIGS. 2A-2G), the filtration chamber outflow 620a, the filtration chamber capillary break 622a, and terminating at the filtration chamber vent 137a via conduit 135a. Also shown in the second flow path is the spectroscopic overflow chamber 618a overlapping with the filtration chamber 634. A third flow path, defined as the plasma flow path, begins at the plasma collection chamber 636, and includes in series the plasma biosensor chamber 672, the plasma spectroscopic inlet transition chamber 614b, the plasma optical chamber 616b, the plasma spectroscopic overflow chamber 618b, the plasma capillary break 622c, and terminating at the plasma vent 137c via a conduit 135c. A conduit 637 is also shown making fluid connection between the plasma biosensor chamber 672 and the plasma spectroscopic inlet transition chamber 614b. Those skilled in the art will appreciate that the conduit 637 can be considered to be a part of the plasma biosensor chamber 672. One plasma biosensor is shown as 652c, which is electrically connected through a medium or electrical conductor 676c to the biosensor electrical output contact 654c. Two whole blood biosensors are shown as 652a and 652b, which are connected to their respective biosensor electrical output contacts 654a and 654b, through respective electrical conductors 676a and 676b. In this embodiment of the apparatus, blood flow is facilitated by the force from a syringe plunger, or the force from blood in a vessel. Blood flows into the inlet open end 612 and towards the blood vents 137a and 137b. Plasma flows from the filtration chamber 634 towards the plasma vent 137c, and the plasma flow is facilitated by capillary action. The capillary break 622c prevents plasma from flowing out of the vent 137c; and capillary breaks 622a and 622b function as buffer chambers for collecting excess blood injected into the apparatus 600d.

Referring collectively to FIGS. 7A-7C, shown are schematic drawings illustrating details of an apparatus 600e that is suitable for both extraction of plasma from a whole blood sample, and whole blood and plasma measurement according to a fifth embodiment of the invention.

Referring to FIG. 7A, shown is a schematic drawing illustrating a side view of an integrated hollow needle and apparatus 600e. The apparatus 600e is considered to be an embodiment of a hollow needle assembly described in U.S. patent application Ser. No. 11/738,889, where the apparatus 600d is considered to be an extension of the hub of the hollow needle 100. The plasma extraction apparatus is identified as 600d, and is similar to the apparatus 600d shown collectively in FIGS. 6A-6E.

FIG. 7B shows a cross-sectional view through the apparatus shown in FIG. 7A along line B-B, and showing parts already identified in FIG. 6E.

FIG. 7C shows a perspective view of the integrated needle and apparatus 600d shown in FIG. 7A. Details of the apparatus 600d are already provided collectively with reference to FIGS. 6A-6E, and further details of the hollow needle 100, showing the sharp open end 147, are provided collectively in FIGS. 8A-8F and FIGS. 10A-10F. Details of the hollow fiber filter bundle identified as 660a are not shown. The integrated needle and apparatus eliminates the need for a traditional syringe.

Referring collectively to FIGS. 8A-8F, shown are schematic drawings illustrating details of a hollow needle 100 that can be used with the apparatus 600d illustrated collectively in FIGS. 6A-6E.

Referring to FIG. 8A, shown is a top view of the hollow needle 100; FIG. 8B shows a left side view of the hollow needle 100 shown in FIG. 8A; FIG. 8C shows a right side view of the hollow needle shown in FIG. 8A; FIG. 8D shows a cross-sectional view through the hollow needle 100 shown in FIG. 8A along line D-D; FIG. 8E shows a perspective view of the hollow needle 100; and FIG. 8F shows an alternative perspective view of the hollow needle 100. Those skilled in the art will appreciate that other suitable mating ends between hollow needle and apparatus can be used, for example without limitations, threaded mating ends, and Luer lock mechanisms. An example is illustrated collectively in FIGS. 19A-19D, where the blunt end of the needle 100b has a female configuration.

Still referring to FIGS. 8A-8F, the needle 100 comprises a shaft 143 and a hub with a front end 139 and a back end 140. It should be understood that the front end refers to a general area of the hub, and does not specifically identify any point or local area. Similarly, it should be understood that the back end refers to a general area of the hub, and does not specifically identify any point or local area. The shaft 143 has a sharp open end 147 and a second end, which is mounted in the passage 145 of the hub at the front end 140. The sharp open end 147 is usually the beveled end of the shaft, which is usually a hollow metal tube. The hollow portion of the shaft 143 is also referred to as the lumen (not shown). The bevel provides a point for piercing a blood vessel. Also shown collectively in FIG. 8A and FIG. 8F is the central axis 133a, which runs through the center of the shaft 143, along its length. The section of the shaft 143 mounted inside the hub is not shown. The passage 145 of the hub is fluidly connected to the lumen of the shaft, and a flow path is defined by the sharp open end 147, which leads into the lumen of the shaft 143, which leads into the passage 145 of the hub, and terminates at a blunt open end 137 of the hub. The blunt open end 137 is located at the back end 140 of the hub. The front end of the hub 139 contains external threads 173 for mating with complementary internal threads 175 in a barrel 200 illustrated collectively in FIGS. 9A-9F, and the blunt open end 137 is housed in a tapered projection 171, which resembles the male end of a syringe. In another embodiment of the hollow needle, for example 100b in FIGS. 19B-19C, the blunt open end 137 is housed in a female configuration of the back end 140 of the hub.

Referring collectively to FIGS. 9A-9F, shown are schematic drawings illustrating details of a barrel 200 for sheathing and unsheathing the shaft 143 of the hollow needle 100 illustrated collectively in FIGS. 8A-8F.

Referring to FIG. 9A, shown is a top view of the barrel 200; FIG. 9B shows a left side view of the barrel 200 shown in FIG. 9A; FIG. 9C shows a first cross-sectional view through the barrel 200 shown in FIG. 9A along line C-C; FIG. 9D shows a right side view of the barrel 200 shown in FIG. 9A; FIG. 9E shows a second cross-sectional view through the barrel 200 shown in FIG. 9A along line E-E; and FIG. 9F shows a perspective view of the barrel 200.

Also illustrated collectively in FIGS. 9A-9F is: an opening 167 in the open anterior end 159 of the barrel 200, for movement of the hollow needle shaft 143; an opening 165 in the open posterior end 161 of the barrel 200, for movement of the back end 140 of the hollow needle hub shown in FIGS. 8A, 8E and 8F; and an axis 133b which runs through the center of the barrel, along the length of the barrel. The barrel 200 comprises an internal chamber 153 for housing the front end 139 of the hub shown in FIGS. 8A, 8E and 8F. The central axis 133a of the hollow needle 100 and axis 133b of the barrel 200 are shown to be coaxial (illustrated in FIG. 10A), but the axes could also be parallel without being coaxial for example, if the outer design of the barrel is not cylindrical. Also shown collectively in FIGS. 9A-9F are internal threads 175 for mating with the external threads 173 in the hub of the needle 100 shown in FIGS. 8A and 8D. In this particular embodiment of the barrel 200, the threads 175 do not run continuously throughout the length of the barrel, and prevents the front end 139 of the hollow needle hub from moving beyond the threaded area in the barrel 200.

Referring collectively to FIGS. 10A-10F, shown are schematic drawings illustrating details of a hollow needle assembly 300 with the hollow needle shaft 143 retracted into the barrel 200.

Referring to FIG. 10A, shown is a top view of the hollow needle assembly 300; FIG. 10B shows a left side view of the hollow needle assembly 300 shown in FIG. 10A; FIG. 10C shows a right side view of the hollow needle assembly 300 shown in FIG. 10A; FIG. 10D shows a cross-sectional view through the hollow needle assembly 300 shown in FIG. 10A along line D-D; FIG. 10E shows a perspective view of the hollow needle assembly 300; and FIG. 10F shows an alternative perspective view of the hollow needle assembly 300. The hollow needle assembly 300 illustrated collectively in FIGS. 10A-10F is an assembly of the hollow needle 100 illustrated collectively in FIGS. 8A-8F, and the barrel 200 illustrated collectively in FIGS. 9A-9F, and accordingly, elements common to these share common reference numerals.

Referring collectively to FIGS. 11A-11C, shown are schematic drawings illustrating details of an apparatus 600f that is suitable for both extraction of plasma from a whole blood sample, and whole blood and plasma measurement according to a sixth embodiment of the invention.

FIG. 11A shows a top view of the apparatus 600f; FIG. 11B is a first cross-sectional view through the apparatus 600f shown in FIG. 11A along line B-B, and FIG. 11C shows a second cross-sectional view through the apparatus 600f shown in FIG. 11A and FIG. 11B along line C-C. The apparatus 600f illustrated collectively in FIGS. 11A-11C is similar to the apparatus illustrated collectively in FIGS. 6A-6E, and accordingly, elements common to them share common reference numerals. The first difference is that apparatus 600f does not have an inlet open end 612 in an inlet chamber 670 that is designed to accommodate the male end of a syringe. Instead, the inlet open end 612 shown collectively in FIGS. 11A and 11C is the open end in a piece of capillary tubing 672. The second difference is that the three flow paths terminate in a single compressible chamber 960d. The third difference is that the distances A and B shown in FIG. 11A are about equal. A meter used to read this apparatus could have a single EMR path or two EMR paths. The apparatus 600d illustrated collectively in FIGS. 6A-6E requires two EMR paths: one for the whole blood optical chamber 616a, and another for the plasma optical chamber 616b, because the optical chambers are not located approximately equidistant from their respective sides of the apparatus 600d, shown as distances A and B in FIG. 11A. The apparatus illustrated collectively in FIGS. 11A-11C could operate with either a single EMR path or two EMR paths, since the distance A is about equal to the distance B, shown in FIG. 11A.

When the apparatus 600f containing sample is inserted into a slot of a meter that provides a single EMR path, the biosensor measurement and one spectroscopic measurement is performed. The spectroscopic measurement is performed either on the blood or on the plasma. In order to perform the second spectroscopic measurement, the apparatus 600f must be removed and flipped over 180 degrees before reinsertion in the meter slot. In an embodiment of a joint-diagnostic spectroscopic and biosensor meter, the software allows the meter to detect whether the sample in the EMR path is plasma or whole blood, and the appropriate spectroscopic algorithm is applied. It must also be noted that the biosensor electrical output contact is not affected after flipping the apparatus 600f, due to the location of the contacts, and the biosensor measurements are preferably performed during the first insertion of the apparatus 600f.

Referring collectively to FIGS. 12A-12D, shown are schematic drawings illustrating details of an example of a joint-diagnostic spectroscopic and biosensor meter 900, required for sample measurement in the apparatus described. In this embodiment of the meter, there is no aperture for channeling the EMR from the EMR source 880 to the sample, and there is an optional lens 870 for focusing EMR emerging from the sample, unto the photodetector included in a part of the meter 900, identified as 890.

Referring to FIG. 12A, shown is a front view of the joint-diagnostic spectroscopic and biosensor meter 900; FIG. 12B is a first cross-sectional view through the joint-diagnostic spectroscopic and biosensor meter 900 shown in FIG. 12A along line B-B, showing the slot 800 as an integral part of the housing 892 of the meter 900; FIG. 12C is a second cross-sectional view through the joint-diagnostic spectroscopic and biosensor meter 900 shown in FIG. 12A along line C-C; and FIG. 12D is a perspective view of the joint-diagnostic spectroscopic and biosensor meter 900, showing the housing 892, a part 890 that includes a photodetector, a display screen 894, and three buttons 882a, 882b and 882c, for manipulating the display functions. The meter slot 800 illustrated collectively in FIGS. 12A-12D is similar to the meter slot 800 illustrated collectively in FIGS. 13A-13C, and accordingly, elements common to them share common reference numerals. The meter slot is designed to accept some embodiments of the present invention.

Referring collectively to FIGS. 13A-13C, shown are schematic drawings illustrating details of the meter slot 800, for a joint-diagnostic spectroscopic and biosensor meter 900 illustrated collectively in FIGS. 12A-12D.

Referring to FIG. 13A, shown is a front view of the meter slot 800; FIG. 13B is a cross-sectional view through the apparatus slot 800 shown in FIG. 13A along line B-B; and FIG. 13C is a perspective view of the meter slot 800. Shown in the slot 800 are two electrical input contacts 854a and 854b, with passages 876a and 876b respectively, for making electrical connections between the contacts 854a and 854b with the meter processor. Also shown are notches 812a and 812b for correct insertion of the apparatus. The measurement apparatus (not shown) for which the slot 800 is designed has ridges than fit in the notches 812a and 812b, and allows electrical connectivity between the measurement apparatus and the meter 900 to be made only when the measurement apparatus is inserted properly in the slot 800.

Referring collectively to FIGS. 14A-14E, shown are schematic drawings illustrating details of an apparatus 600g that is suitable for both extraction of plasma from a whole blood sample, and plasma measurement according to a seventh embodiment of the invention.

FIG. 14A shows a top view of the apparatus 600g, FIG. 14B shows a first cross-sectional view through the apparatus 600g shown in FIG. 14A along line B-B, FIG. 14C shows a second cross-sectional view through the apparatus 600g shown in FIG. 14A and FIG. 14B along line C-C, FIG. 14D shows a perspective view of the apparatus 600g, and FIG. 14E shows an alternative perspective view of the apparatus 600g. The apparatus 600g illustrated collectively in FIGS. 14A-14E is similar to the apparatus illustrated collectively in FIGS. 1A-31D, and accordingly, elements common to them share common reference numerals. The first difference is the inlet open end 612 is housed in a flared inlet chamber 670, instead of a piece of capillary tubing 672 shown in FIGS. 1A and 1D. The second difference is the blood flow path terminates at a vent 137a. The third difference is the plasma measurement method is spectroscopic.

In a first method of use, the flexible members 962a and 962b of the compressible chamber 960c are squeezed to dispel air, and then the male end of a syringe containing blood is inserted into the inlet chamber 670. Before releasing the flexible members 962a and 962b of the compressible chamber 960c, blood is slowly injected into the apparatus 600g until it passes the hollow fiber filter 660a. The flexible members 962a and 962b of the compressible chamber are then released while injection of blood into the apparatus continues slowly. Those skilled in the art will appreciate that the sizes of the internal chambers could be optimized so that the plasma optical chamber 616b is full by the time the blood arrives at the capillary break 622a. In this embodiment, the capillary break functions as a buffer chamber for excess blood, to prevent any blood from escaping through the vent 137a. The apparatus 600g is constructed with material that allows the user to see the blood and plasma in their respective flow paths. In some embodiments, the apparatus includes at least one visible guide line, preferably after the hollow fiber filter 660a, to indicate that the flexible members 962a and 962b of the compressible chamber must be released.

In a second method of use, the skin of the patient is pricked with a lancet (also referred to as a pin prick), and a blood drop is allowed to form on the skin. After the flexible members 962a and 962b of the compressible chamber 960c are squeezed to dispel air, the inlet open end 612 of the apparatus 600g is placed over the drop of blood, creating a seal between the skin and the inlet open end 612, and blood is gently squeezed into the apparatus 600g, as if blood was injected into the apparatus from a syringe. The flexible members 962a and 962b of the compressible chamber 960c are then released, and blood is allowed to flow into the blood flow path. The procedure will have to be repeated if blood flow is insufficient. Preferably, the site of the pin prick is warmed with a mild heating pad for a few minutes, before the skin is pricked again. Warming the skin promotes blood flow.

Referring collectively to FIGS. 15A-15E, shown are schematic drawings illustrating details of a combined apparatus and cap 600k, suitable for both extraction of plasma from a whole blood sample, and plasma measurement according to an eight embodiment of the invention. The combined apparatus and cap 600k comprises an apparatus 600h that is suitable for both extraction of plasma from a whole blood sample and plasma measurement according to an eight embodiment of the invention, and a cap 960. The cap 960 comprises a tether 964 and a retaining ring 966, used to tether the cap 960 to the apparatus 600h.

FIG. 15A is a schematic drawing showing details of the top view of combined apparatus and cap 600k, FIG. 15B shows a first cross-sectional view through the combined apparatus and cap 600k shown in FIG. 15A along line B-B, FIG. 15C shows a second cross-sectional view through the combined apparatus and cap 600k shown in FIG. 15A and FIG. 15B along line C-C, FIG. 15D shows a perspective view of the combined apparatus and cap 600k, and FIG. 15E shows an alternative perspective view of the combined apparatus and cap 600k.

Apparatus 600h illustrated collectively in FIGS. 15A-15E is similar to the apparatus illustrated collectively in FIGS. 4A-4D, and accordingly, elements common to them share common reference numerals. The first difference is that the filtration chamber comprises a hollow fiber filter bundle 660a, illustrated in details collectively in FIGS. 2A-2G. The second difference is that the inlet open end 612 is housed in an extended piece of capillary tubing 672b. The extended piece of capillary tubing 672b is particularly useful for reaching into a microtube containing anticoagulated blood, for bilirubin measurement, which is useful for diagnosis and for monitoring treatment of neonatal jaundice.

In use, the flexible members 962a and 962b of the compressible chambers 960a and 960b are squeezed to dispel air from the apparatus 600h. Then the inlet open end 612 is submerged into anticoagulated blood contained in a microtube. Keeping the inlet open end 612 submerged in the blood, the flexible members 962a and 962b of the compressible chamber are released, drawing blood into the blood flow path, and subsequently drawing plasma into the plasma flow path. Those skilled in the art will appreciate that the rebound in the flexible members 962a and 962b, the relative sizes of the compressible chambers 960*a* and 960*b*, and the sizes of the different sections of the flow paths could be optimized for efficient blood flow and plasma extraction.

Since the only open end in the apparatus 600*h* is the inlet open end 612, the cap 960 is useful to prevent blood contamination.

Those skilled in the art will appreciate that the housing of the apparatus described can be manufactured in two halves, a top half and a bottom half, and they could be assembled together by glue or ultrasonic welding. For illustration, FIG. 14D is a perspective view of the top half of apparatus 600*g*, and FIG. 14E is a perspective view of the bottom half of apparatus 600*g*. Those skilled in the art will also appreciate that the hollow fiber filter bundle 660*a* shown in FIG. 14C, can be made separately and sandwiched between the two halves during assembly, so that the housing fits tightly around the flanges 682 and 684 (FIGS. 2E and 2G), sealing the flanges at their periphery, and maintaining a barrier between the blood compartment and the plasma compartment.

The ninth, tenth and eleventh embodiments of the invention illustrated collectively in FIGS. 16A-20D, are suitable for extraction of plasma from whole blood, and removal of the plasma for analysis by other means, and will share similar reference numerals common to apparatus already described. In order to distinguish the various embodiments of the invention, letters are sometimes appended to the reference numerals. Those skilled in the art will appreciate that certain features already described for the first eight embodiments of the invention, can be combined with the next three embodiments of the invention for the inventive solution.

Referring collectively to FIGS. 16A-16D, shown are schematic drawings illustrating details of an apparatus 600*m* suitable for extraction of plasma from whole blood, according to a ninth embodiment of the invention. Specifically, FIG. 16A is a schematic drawing illustrating the top view of an apparatus 600*m*. FIG. 16B shows a first cross-sectional view through the apparatus 600*m* shown in FIG. 16A along line B-B, FIG. 16C shows a second cross-sectional view through the apparatus 600*m* shown in FIG. 16A and FIG. 16B along line C-C, and FIG. 16D shows a perspective view of the apparatus 600*m* shown in FIG. 16A. The apparatus 600*m* includes a housing 123 defining a blood flow path from an open end 612 to an open end 620*d*, and a plasma collection chamber 636, fluidly connected to an open end 620*e*. The blood flow path includes a filtration chamber 634, comprising a hollow fiber filter bundle 660*c*, and fluidly connected to the open ends 612 and 620*d*. The hollow fiber filter bundle 660*c* is similar to the hollow fiber filter bundle 660*a* illustrated collectively in FIGS. 2A-2G, and accordingly, elements common to both share common reference numerals. The primary difference in the hollow fiber filter bundle 660*c* is that both flanges (shown as 682 and 684 in FIGS. 2A, 2E and 2G) in the hollow fiber filter bundle 660*c* are perforated, but those skilled in the art will appreciate that only the flange adjacent to the plasma collection chamber 636 needs to be perforated, in order to fluidly connect the lumen (shown as 692 in FIG. 5E) of the hollow fiber filter, of the hollow fiber filters in the hollow fiber filter bundle 660*c*, to the plasma collection chamber 636. The second difference is that the flanges in fiber filter bundle 600*c* are circular, which is not essential. The walls of the hollow fiber filter (shown as 694 in FIG. 5E), collectively form a barrier between whole blood and plasma extracted from the blood. In this specific embodiment of the invention, the plasma collection chamber 636 is fluidly connected to the lumen (shown as 692 in FIG. 5E) of the hollow fiber filters, and also fluidly connected to an open end 620*e*. The open end 620*d* is fluidly connected to a chamber 637*d*, designed to accommodate the male end of a syringe 970*b*, illustrated in FIGS. 20B and 20D. The open end 620*e* is fluidly connected to a chamber 637*e*, designed to accommodate the male end of a syringe 970*a*, illustrated in FIGS. 20C and 20D. The blood flow means, plasma extraction means, and plasma removal means for the apparatus 600*m* are provided by two syringes 970*a* and 970*b* illustrated collectively in FIGS. 20A-20D. Therefore, syringes 970*a* and 970*b* are considered to be part of the ninth embodiment of the invention.

Referring collectively to FIGS. 20A-20D, shown are schematic drawings illustrating details of the apparatus 600*m*, fitted with two syringes 970*a* and 970*b*. Syringe 970*b* provides blood flow means, and syringe 970*a* provides plasma extraction and plasma removal means. FIG. 20A is a top view, FIG. 20B is a first cross-sectional view through the apparatus 600*m* (and the syringe 970*b*) shown in FIG. 20A along line B-B, FIG. 20C is a second cross-sectional view through the apparatus 600*m* (and the syringe 970*a*) shown in FIG. 20A along line C-C, and FIG. 20D is a third cross-sectional view through the apparatus 600*m* (and the syringes 970*a* and 970*b*) shown in FIG. 20A and FIG. 20B along line D-D. The apparatus 600*m* is the same apparatus 600*m* illustrated collectively in FIGS. 16A-16D, and accordingly, share common reference numerals for identifying certain elements of the apparatus 600*m*. Syringe 970*b* is used to provide blood flow means, by either a) injecting blood into the filtration chamber 634 (positive pressure), vented at the open end 612, or b) creating a negative pressure in the syringe 970*b* by withdrawing the plunger, while the open end 612 is in full contact with the blood supply. Those skilled in the art will appreciate that the open end 612 functions as an outlet open end or a vent, when positive pressure is used for the blood flow means, and the same open end 612 functions as an inlet open end when negative pressure is used for the blood flow means. The open end 612 can also be in contact with the blood, by engaging a hollow needle at the male projection 672*c* of the apparatus 600*m*. A non-limiting example of a hollow needle that can be used with apparatus 600*m* is a hollow needle assembly 300*b*, illustrated collectively in FIGS. 19A-19D. In another embodiment of the invention, the hollow needle 100 is integrated with the apparatus 600*m*, as illustrated in the fifth embodiment of the invention, illustrated collectively in FIGS. 7A-7C. In this specific embodiment of the invention, illustrated collectively in FIGS. 7A-7C, the inlet open end 612 (shown in FIG. 20A) is replaced by the sharp open end 147, shown in FIGS. 7B and 7C, and FIGS. 19A and 19D.

Referring collectively to FIGS. 19A-19D, shown are schematic drawings illustrating details of the apparatus 600*m*, fitted with a hollow needle assembly 300*b*. FIG. 19A shows the top view, FIG. 19B shows a first cross-sectional view through the apparatus 600*m* (and the hollow needle assembly 300*b*) shown in FIG. 19A along line B-B, FIG. 19C shows a second cross-sectional view through the apparatus 600*m* (and the hollow needle 300*b*) shown in FIG. 19A and FIG. 19B along line C-C, and FIG. 19D shows a perspective view of the apparatus 600*m* (and the hollow needle assembly 300*b*) shown in FIG. 19A. The apparatus 600*m* is the same apparatus 600*m* illustrated collectively in FIGS. 16A-16D, and accordingly, share common reference numerals for identifying certain elements of the apparatus 600*m*. The hollow needle assembly 300*b* illustrated collectively in FIGS. 19A-19D is similar to the hollow needle assembly 300 illustrated collectively in FIGS. 10A-10F, and accordingly, elements common to both share common reference numerals. The only difference is that the outlet 137 (shown in FIGS. 8D and 8F) is housed in a female configuration of the back end 140 of the hub of the hollow needle. The hollow needle of the hollow needle assembly 300 is illustrated collectively in FIGS. 8A-8F, and the barrel of the hollow needle assembly 300 is illustrated collectively in FIGS. 9A-9F. When a sharp inlet open end is required, for example, if the blood is supplied by a vessel that needs to be pierced, then the hollow needle assembly 300b (illustrated collectively in FIGS. 19A-19D), as well as the two syringes 970a and 970b (illustrated collectively in FIGS. 20A-20D) are considered to be part of the ninth embodiment of the invention.

Figure 17D:
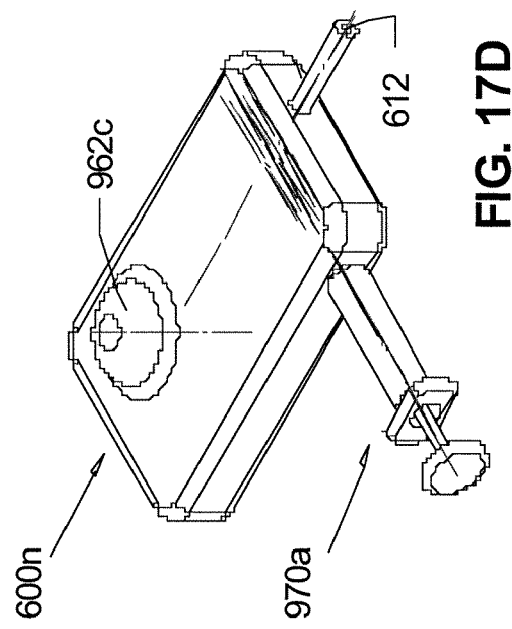
FIG. 17D is a perspective view of the apparatus 600n (and the syringe 970a) shown in FIG. 17A.
Figure 17A:
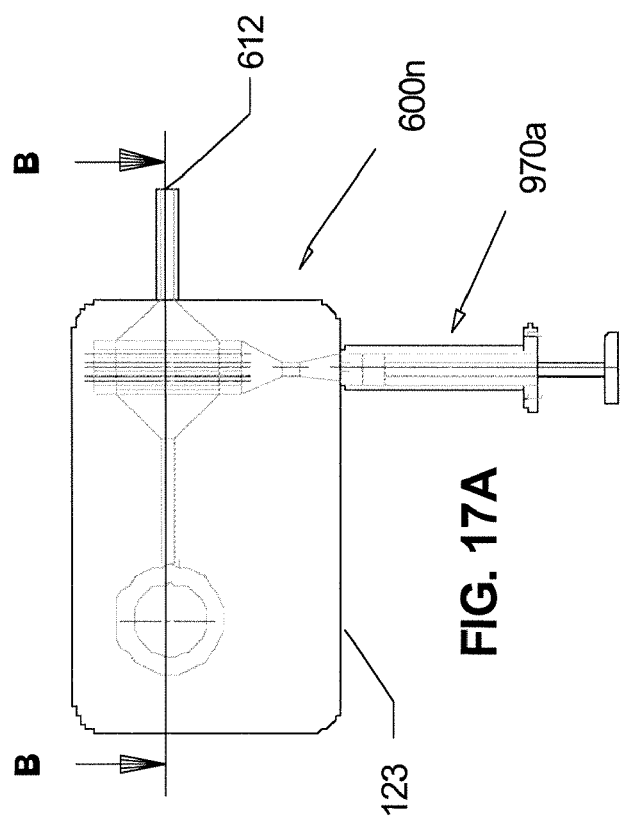
FIG. 17A is a schematic drawing showing details of the top view of an apparatus 600n (with a syringe 970a attached) suitable for extraction of plasma from whole blood, according to a tenth embodiment of the invention.
Figure 17B:
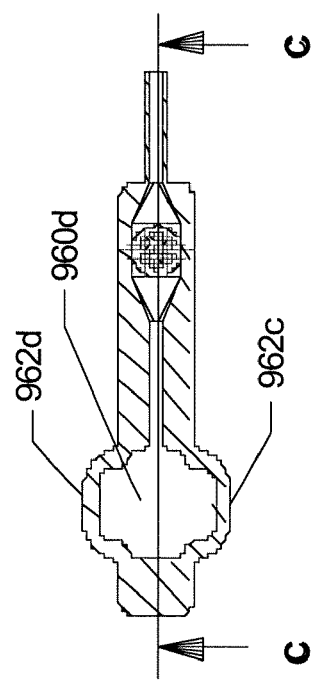
FIG. 17B is a first cross-sectional view through the apparatus 600n shown in FIG. 17A along line B-B.

Referring collectively to FIGS. 17A-17D, shown are schematic drawings illustrating details of an apparatus 600n, fitted with a syringe 970a, suitable for extraction of plasma from whole blood, according to a tenth embodiment of the invention. Specifically, FIG. 17A shows a top view of the apparatus 600n, FIG. 17B shows a first cross-sectional view through the apparatus 600n shown in FIG. 17A along line B-B, FIG. 17C shows a second cross-sectional view through the apparatus 600n (and the syringe 970a) shown in FIG. 17A and FIG. 17B along line C-C, and FIG. 17D shows a perspective view of the apparatus 600n (and the syringe 970a) shown in FIG. 17A. The apparatus 600n illustrated collectively in FIGS. 17A-17D is similar to the apparatus 600m illustrated collectively in FIGS. 16A-16D, and accordingly, elements common to both share common reference numerals. The primary difference, illustrated collectively in FIGS. 17A-17D, is in the blood flow path, described as follows: a) the open end 612 is housed In a piece of capillary tubing 672d, and b) the filtration chamber is fluidly connected to a compressible chamber 960d, instead of an open end 620d shown in FIGS. 16A and 16C. With specific reference to FIG. 17b, the top flexible member 962c and the bottom flexible member 962d of the housing 123 define the compressible chamber 960d. For greater clarity, a perspective view of the top flexible member 962c is provided in FIG. 17D. Specifically in the apparatus 600n, the open end 612 is an inlet open end, and the blood flow means includes squeezing the compressible members 962c and 962d between the thumb and forefinger in order to dispel air from the compressible chamber 960d, inserting the inlet open end 612 into the blood supply, and releasing the flexible members 962d and 962c to create negative pressure within the compressible chamber 960d. Preferably the housing 123 is transparent or translucent, in order to see the blood flow. In use, the male end of the syringe 970a, with its plunger pushed in, is inserted in the chamber 637e before the blood flow is initiated, in order to provide the plasma extraction means. The plasma extraction means is initiated by slowly pulling the plunger of the syringe 970a outward, creating negative pressure in the plasma collection chamber 636. Preferably, the plunger of the syringe 970a is not pulled out all the way because further pull on the plunger may be required to remove the plasma from the housing 123 of the apparatus. The plasma extraction means is preferably initiated when the hollow fiber filters are seen surrounded by whole blood. After the flexible members are restored to their original shape, the plasma in the plasma collection chamber is aspirated into the syringe, and the syringe containing plasma is detached from the apparatus 600n. In this specific embodiment, the syringe 970a also provides plasma removal means, and the plasma in the syringe is analyzed on a different apparatus. Those skilled in the art will appreciate that the length of the piece of capillary tube 672d must be long enough to access the blood sample, and also the open end 612 can be housed in a projection like 672c illustrated collectively in FIGS. 16A-16D, instead of the piece of capillary tube 672d.

Referring collectively to FIGS. 18A-18D, shown are schematic drawings illustrating details of an apparatus 600p, fitted with a cap 960b attached, suitable for extraction of plasma from whole blood, according to an eleventh embodiment of the invention. Specifically, FIG. 18A shows a top view, FIG. 18B shows a first cross-sectional view through the apparatus 600p shown in FIG. 18A along line B-B, FIG. 18C shows a second cross-sectional view through the apparatus 600p shown in FIG. 18A and FIG. 18B along line C-C, and FIG. 18D shows a perspective view of the apparatus 600p shown in FIG. 18A. The apparatus 600p is similar to the apparatus 600m illustrated collectively in FIGS. 16A-16D, and accordingly, elements common to both share common reference numerals. The primary difference is that syringes are not required for blood flow means, plasma extraction means, or plasma removal means. The other differences will become obvious when the method of use is described.

Still referring to the apparatus 600p, illustrated collectively in FIGS. 18A-18D, the blood flow path begins at an open end 612, and terminates at a compressible chamber 960d. In this particular embodiment, the protrusion 672c resembles the male end of a syringe, and houses the inlet open end 612. The inlet open end 612 is fluidly connected with the inlet transition chamber 670. Those skilled in the art will appreciate that the inlet transition chamber 670 simply serves to identify the internal portion of the protrusion 672c, and could be considered as part of the filtration chamber 634. The filtration chamber 634 is fluidly connected with the compressible chamber 960d and the inlet open end 612. A needle may be fitted on the protrusion 672c that houses the open end 612, if blood is to be drawn from a vessel, for example, a blood vessel. An example of a needle fitted on the protrusion 672c is illustrated collectively in FIGS. 19A-19D as 300b. In this particular embodiment, a short conduit 637b fluidly connects the filtration chamber 634 with the compressible chamber 960d. Those skilled in the art will appreciate that the conduit 637b could be considered to be a part of the filtration chamber 634, and is not essential. The compressible chamber 960d is defined by two flexible members 962c and 962d, and by pressing and releasing the flexible members 962c and 962d, negative pressure created inside the compressible chamber 960d provides blood flow means for passing blood along the outside of the hollow fiber filters. The outside of the hollow fiber filters is also referred to as the blood side of the porous membrane, and the inside of the of the hollow fiber filters defining the lumen (shown as 692 in FIG. 5E) of the hollow fiber filters, is referred to as the plasma side of the porous membrane. The plasma extraction means include negative pressure provided by a second compressible chamber 960e. The compressible chamber 960e is defined by two flexible members 962e and 962f, and by pressing and releasing the flexible members 962e and 962f, negative pressure created inside the compressible chamber 960e pulls plasma from the blood side of the membrane to the plasma side, and into the plasma collection chamber 636, also referred to as plasma extraction. The apparatus 600p is also fitted with a piece of capillary tubing 673, with an open end 675 and a passage 636c, which fluidly connect the open end 675 with the plasma collection chamber 636. Those skilled in the art will appreciate that the passage 636c could be considered to be a part of the plasma collection chamber 636. Moreover, the protrusions 673 and 672c may be configured in any shape, as illustrated without limitations, in other embodiments of the invention. In this particular embodiment, the open end 675 is fitted with a removable cap 960b that is considered to be part of the apparatus 600p, and the porous membrane is configured in the form of a hollow fiber filter bundle 660c, with perforated flanges on both ends.

In operation of the apparatus 600p, the cap 960b is initially engaged, to seal the open end 675, shown in FIG. 18C. In this specific embodiment, the male projection 672c is fitted onto a hollow needle (for example without any limitations, the hollow needle assembly 300b illustrated collectively in FIGS. 19A-19D). With the cap 960b and hollow needle assembly 300b attached to the body 123 of the apparatus 600p, the flexible members 962c and 962d, and the flexible members 962e and 962f are compressed simultaneously between the thumb and forefinger, to dispel air out of the blood flow path and the plasma collection chamber, through the sharp open end of the hollow needle (for example, 147 illustrated collectively in FIGS. 19A-19D). The sharp open end 147 of the hollow needle assembly (illustrated collectively in FIGS. 19A-19D) is then is inserted in the blood supply. Those skilled in the art will appreciate that the blood supply includes without any limitations, a blood vessel, an arterial blood line, a venous blood line, and a tube (for example, a vacutainer tube). By releasing the flexible members 962c, 962d, 962e, and 962f, blood flow means and plasma extraction means are initiated. Those skilled in the art will appreciate that the draw from the compressible chambers 960d and 960e, and the rebound of the flexible members 962c, 962d, 962e and 962f could be optimized, so that the flexible members can be totally released, allowing the shape of the flexible members can be restored at appropriate speeds. In a particular embodiment, the draw from the compressible chamber 960d is greater than the draw from the compressible chamber 960e, enabling the hollow fiber filters to be surrounded by blood before the plasma extraction is initiated. Specifically, in the apparatus 600p, the compressible chambers 960d and 960e are in close proximity so that they can be squeezed simultaneously with one hand, and also either one of the compressible chambers 960d or 960e could be squeezed selectively.

Still referring to the operation of the apparatus illustrated collectively in FIGS. 18A-18D, plasma removal from the body 123 of the apparatus 600p is preferably initiated after the flexible members are restored to their original shape. The plasma removal means include the following steps: a) removing the cap 960b, and preferably but not essential, placing the cap over the open end 612; and b) squeezing the flexible members 962e and 962f of the compressible chamber 960e, to dispel at least some of the plasma from the plasma collection chamber 636. The plasma could be dispelled directly into a measuring device, or in a tube for plasma analysis at any time later. Alternatively, the plasma could be stored in the body 123 of the apparatus 600p for analysis at any time later, preferably with the open ends 612 and 675 capped. Those skilled in the art will appreciate that the protrusions 673 and 672c can be have the same shape, but even if the shapes were different as in the specific example illustrated collectively in FIGS. 18a-18D, the cap 960b could be designed to seal the open ends 675 and 612 of the protrusions 673 and 672c respectively.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

The invention claimed is:

1. A system for extracting plasma from blood received from a blood supply, the system comprising:
a housing;
an inlet opening in the housing for receiving the blood;
a blood flow path in the housing beginning at the inlet opening and terminating at one of a blood flow path outlet and a blood flow path compression chamber for facilitating a blood flow in the blood flow path;
a filtration chamber within the housing for receiving the blood from the inlet opening, the filtration chamber comprising a membrane separating the blood flow path from a plasma compartment, wherein the blood flow path intersects with the filtration chamber at a fluid intersection;
a plasma flow path beginning at the plasma compartment and terminating at a manually operable plasma flow path compression chamber for pulling the plasma across the membrane from the blood flow path to the plasma compartment, wherein the plasma flow path compression chamber defines a cavity, at least a portion of the cavity being located within the housing.

2. The system according to claim 1, wherein the membrane for separating the blood flow path from the plasma compartment comprises at least one hollow fiber filter.

3. The system according to claim 2, wherein the at least one hollow fiber filter is assembled between two flanges, and at least one of the two flanges is perforated.

4. The system according to claim 2, wherein at the fluid intersection of the blood flow path and the filtration chamber, a direction of the blood flow defined by the blood flow path is approximately orthogonal to the longitudinal axis of the at least one hollow fiber filter, and wherein the plasma compartment includes the inside of the at least one hollow fiber filter.

5. The system according to claim 2, wherein at the fluid intersection of the blood flow path and the filtration chamber, a direction of the blood flow defined by the blood flow path is approximately parallel to the longitudinal axis of the at least one hollow fiber filter, and wherein the plasma compartment includes the outside of the at least one hollow fiber filter.

6. The system according to claim 1, wherein
the blood flow path terminates at the blood flow path compression chamber, and
the blood flow path compression chamber and the plasma flow path compression chamber are fluidly connected to one another.

7. The system according to claim 1, wherein
the manually operable plasma flow path compression chamber comprises at least one flexible member that is manually operable to reduce a volume of the cavity, the cavity being at least partially enclosed by the at least one flexible member.

8. The system according to claim 1, wherein
the manually operable plasma flow path compression chamber comprises a first member and a second member, the cavity extends between the first member and the second member, the first member is flexible and is located substantially opposite the second member, the first member is manually squeezable to move toward the second member, and after being moved toward the second member the first member is resiliently biased to move away from the second member to generate a negative pressure in the plasma compartment.

9. The system according to claim 1, wherein the plasma flow path further comprises at least one of an optical chamber and a biosensor, wherein
the at least one optical chamber comprises at least one optical wall-portion to facilitate detection of an EMR-based signal derived from the plasma for measuring at least one plasma analyte, and wherein the at least one biosensor is in electrical communication with an electrical output located on an external surface of the housing, the electrical output being operable to receive plasma biosensor data from the biosensor in the plasma flow path and to transmit the plasma biosensor data to an analysis meter.

10. The system according to claim 9, wherein the at least one optical chamber further comprises a reflective coating on one of the at least one optical wall-portion.

11. The system according to claim 1, wherein the blood flow path further comprises at least one of an optical chamber and a biosensor, wherein
the at least one optical chamber comprises at least one optical wall-portion to facilitate detection of an EMR-based signal derived from the blood for measuring at least one blood analyte, and wherein
the at least one biosensor is in electrical communication with an electrical output located on an external surface of the housing, the electrical output being operable to receive blood biosensor data from the biosensor in the blood flow path and to transmit the blood biosensor data to an analysis meter.

12. The system according to claim 1, wherein one of the inlet opening and the blood flow path outlet is configured to engage a syringe for facilitating the blood flow in the blood flow path.

13. The system according to claim 1, wherein the blood flow path outlet is a vent that provides an outflow path for air.

14. A system for extracting plasma from blood, comprising:
a housing;
an inlet opening in the housing for receiving the blood;
a blood flow path beginning at the inlet opening and terminating at a manually operable blood flow path compression chamber for facilitating a blood flow in the blood flow path, wherein the blood flow path compression chamber defines a cavity, at least a portion of the cavity being located within the housing;
a filtration chamber within the housing for receiving the blood from the inlet opening, the filtration chamber comprising a membrane separating the blood flow path from a plasma compartment, wherein the blood flow path intersects with the filtration chamber at a fluid intersection; and
a first plasma flow path beginning at the plasma compartment and terminating at one of a first plasma flow path outlet and a first plasma flow path compression chamber for drawing the plasma across the membrane, from the blood flow path to the plasma compartment.

15. The system according to claim 8, wherein the membrane separating the blood flow path from the plasma compartment comprises at least one hollow fiber filter.

16. The system according to claim 15, wherein the at least one hollow fiber filter is assembled between two flanges, and at least one of the two flanges is perforated.

17. The system according to claim 15, wherein at the fluid intersection of the blood flow path and the filtration chamber, a direction of the blood flow defined by the blood flow path is approximately orthogonal to the longitudinal axis of the at least one hollow fiber filter, and wherein the plasma compartment includes the inside of the at least one hollow fiber filter.

18. The system according to claim 15, wherein at the fluid intersection of the blood flow path and the filtration chamber, a direction of the blood flow defined by the blood flow path is approximately parallel to the longitudinal axis of the at least one hollow fiber filter, and wherein the plasma compartment includes the outside of the at least one hollow fiber filter.

19. The system according to claim 14, wherein
the first plasma flow path terminates at the first plasma flow path compression chamber, and
the first plasma flow path compression chamber and the blood flow path compression chamber are fluidly connected to one another.

20. The system according to claim 14, wherein
the manually operable blood flow path compression chamber comprises at least one flexible member that is manually operable to reduce a volume of the cavity, the cavity being at least partially enclosed by the at least one flexible member.

21. The system according to claim 14, wherein
the manually operable blood flow path compression chamber comprises a first member and a second member, the cavity extends between the first member and the second member, the first member is flexible and is located substantially opposite the second member, the first member is manually squeezable to move toward the second member, and after being moved toward the second member the first member is resiliently biased to move away from the second member to generate a negative pressure in the blood flow path.

22. The system according to claim 14, wherein the first plasma flow path further comprises at least one of an optical chamber and a biosensor, wherein
the at least one optical chamber comprises at least one optical wall-portion to facilitate detection of an EMR-based signal derived from the plasma for measuring at least one plasma analyte of the plasma in the plasma flow path, and wherein
the at least one biosensor is in electrical communication with an electrical output located on an external surface of the housing, the electrical output being operable to receive plasma biosensor data from the biosensor in first plasma flow path to transmit the plasma biosensor data to an analysis meter.

23. The system according to claim 22, wherein the at least one optical chamber further comprises a reflective coating on one of the at least one optical chamber wall-portion.

24. The system according to claim 14, wherein the blood flow path further comprises at least one of an optical chamber and a biosensor, wherein
the at least one optical chamber comprises at least one optical wall-portion to facilitate detection of an EMR-based signal derived from the blood for measuring at least one blood analyte of the blood in the blood flow path, and wherein
the at least one biosensor is in electrical communication with an electrical output located on an external surface of the housing, the electrical output being operable to receive blood biosensor data from the biosensor in the blood flow path and to transmit the blood biosensor data to an analysis meter.

25. The system according to claim 14, further comprising:
a second plasma flow path beginning at the plasma compartment and terminating at a second plasma flow path outlet; and
a cap, wherein
the first plasma flow path terminates at the first plasma flow path compression chamber, and
when the cap covers the second plasma flow path outlet, the second plasma flow path outlet is in a closed state for impeding plasma flow out of the plasma compartment via the second plasma flow path outlet, and wherein when the cap is removed from the second plasma flow path outlet, the second plasma flow path outlet is in an open state for facilitating plasma flow out of the plasma compartment via the second plasma flow path outlet, and wherein when the second plasma flow path outlet is in the closed state, the first plasma flow path compression chamber is operable to generate a negative pressure in the plasma compartment to draw the plasma across the membrane, from the blood flow path to the plasma compartment, and when the second plasma flow path outlet is in the open state, the first plasma flow path compression chamber is operable to push at least some of the plasma out of the plasma compartment via the second plasma flow path outlet.

26. The system according to claim 14, wherein the first plasma flow path outlet is configured to engage a syringe, the syringe is operable to generate a negative pressure in the plasma compartment to draw the plasma across the membrane, from the blood flow path to the plasma compartment.

* * * * *

UNITED STATES PATENT AND TRADEMARK OFFICE
CERTIFICATE OF CORRECTION

| | | |
|---|---|---|
| PATENT NO. | : 7,807,450 B2 | |
| APPLICATION NO. | : 11/835631 | |
| DATED | : October 5, 2010 | |
| INVENTOR(S) | : James Samsoondar | |

It is certified that error appears in the above-identified patent and that said Letters Patent is hereby corrected as shown below:

Col. 31, line 50 incorrectly recites, "The system according to claim 8". This phrase in line 50 should read, "The system according to claim 14".

Signed and Sealed this
Tenth Day of May, 2011

David J. Kappos
*Director of the United States Patent and Trademark Office*